United States Patent
Barrall et al.

(10) Patent No.: US 10,577,653 B2
(45) Date of Patent: Mar. 3, 2020

(54) COUNTERACTING OSMOTIC IMBALANCE IN A SEQUENCING CELL

(71) Applicant: Roche Sequencing Solutions, Inc., Pleasanton, CA (US)

(72) Inventors: Geoffrey Barrall, San Diego, CA (US); Jason Komadina, Fremont, CA (US); Marcin Rojek, Sunnyvale, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 188 days.

(21) Appl. No.: 15/630,342

(22) Filed: Jun. 22, 2017

(65) Prior Publication Data

US 2017/0369944 A1 Dec. 28, 2017

Related U.S. Application Data

(60) Provisional application No. 62/355,114, filed on Jun. 27, 2016.

(51) Int. Cl.
| | | |
|---|---|---|
| *C12Q 1/6874* | (2018.01) | |
| *C12Q 1/6869* | (2018.01) | |
| *G01N 27/447* | (2006.01) | |
| *G01N 33/487* | (2006.01) | |

(52) U.S. Cl.
CPC ......... *C12Q 1/6874* (2013.01); *C12Q 1/6869* (2013.01); *G01N 27/44782* (2013.01); *G01N 27/44791* (2013.01); *G01N 33/48721* (2013.01)

(58) Field of Classification Search
None
See application file for complete search history.

(56) References Cited

U.S. PATENT DOCUMENTS

| | | |
|---|---|---|
| 9,557,294 B2 | 1/2017 | Chen et al. |
| 2014/0034497 A1 | 6/2014 | Davis et al. |
| 2015/0152492 A1* | 6/2015 | Brown et al. ........ C12Q 1/6869 435/6.1 |
| 2016/0178554 A1 | 6/2016 | Chen et al. |

FOREIGN PATENT DOCUMENTS

| | | |
|---|---|---|
| WO | 2012/095660 A2 | 7/2012 |
| WO | 2015/061510 A1 | 4/2015 |

OTHER PUBLICATIONS

International search report and written opinion dated Sep. 4, 2017 in corresponding PCT application No. PCT/EP2017/065626 filed on Jun. 26, 2017.
Gu, Li-Qun, et al., "Electroosmotic enhancement of the binding of a neutral molecule to a transmembrane pore," Proceedings National Academy of Sciences PNAS, National Academy of Sciences, US, vol. 100, No. 26 (Dec. 23, 2003) (pp. 15498-15503).
International Search Report dated Aug. 22, 2017 and the Written Opinion of the International Searching Authority corresponding to International Application PCT/EP2017/065782 (eleven pages).
Noskov, S. Y., et al.; "Ion Permeation through the [alpha]-Hemolysin Channel: Theoretical Studies Based on Brownian Dynamics and Poisson-Nernst-Plank Electrodiffusion Theory"; *Biophysical Journal* ; vol. 87, No. 4; Oct. 2004; pp. 2299-2309.
Schibel, A. E. P., et al.; "Fluorescence Microscopy of the Pressure-Dependent Structure of Lipid PLBs Suspended across Conical Nanopores"; *Journal of the American Chemical Society*; vol. 133, No. 20; 2011; pp. 7810-7815.
U.S. Appl. No. 15/085,700 entitled "Non-Destructive Bilayer Monitoring Using Measurement of Bilayer Response to Electrical Stimulus" filed Mar. 30, 2016.
U.S. Appl. No. 15/085,713 entitled "Electrical Enhancement of Bilayer Formation" filed Mar. 30, 2016.

* cited by examiner

*Primary Examiner* — Kaijiang Zhang
(74) *Attorney, Agent, or Firm* — Kilpatrick Townsend and Stockton LLP

(57) ABSTRACT

A method of analyzing a molecule is disclosed. A lipid bilayer is formed such that it divides a first reservoir characterized by a first reservoir osmolarity from a second reservoir characterized by a second reservoir osmolarity. An electrolyte solution is flowed to the first reservoir that tends to make a first change to a ratio of the first reservoir osmolarity to the second reservoir osmolarity. A voltage is applied across the lipid bilayer, wherein the lipid bilayer is inserted with a nanopore, and wherein a net transfer of ions between the first reservoir and the second reservoir tends to make a second change to the ratio of the first reservoir osmolarity to the second reservoir osmolarity, and wherein the first change to the ratio and the second change to the ratio tends to counter-balance each other.

14 Claims, 16 Drawing Sheets

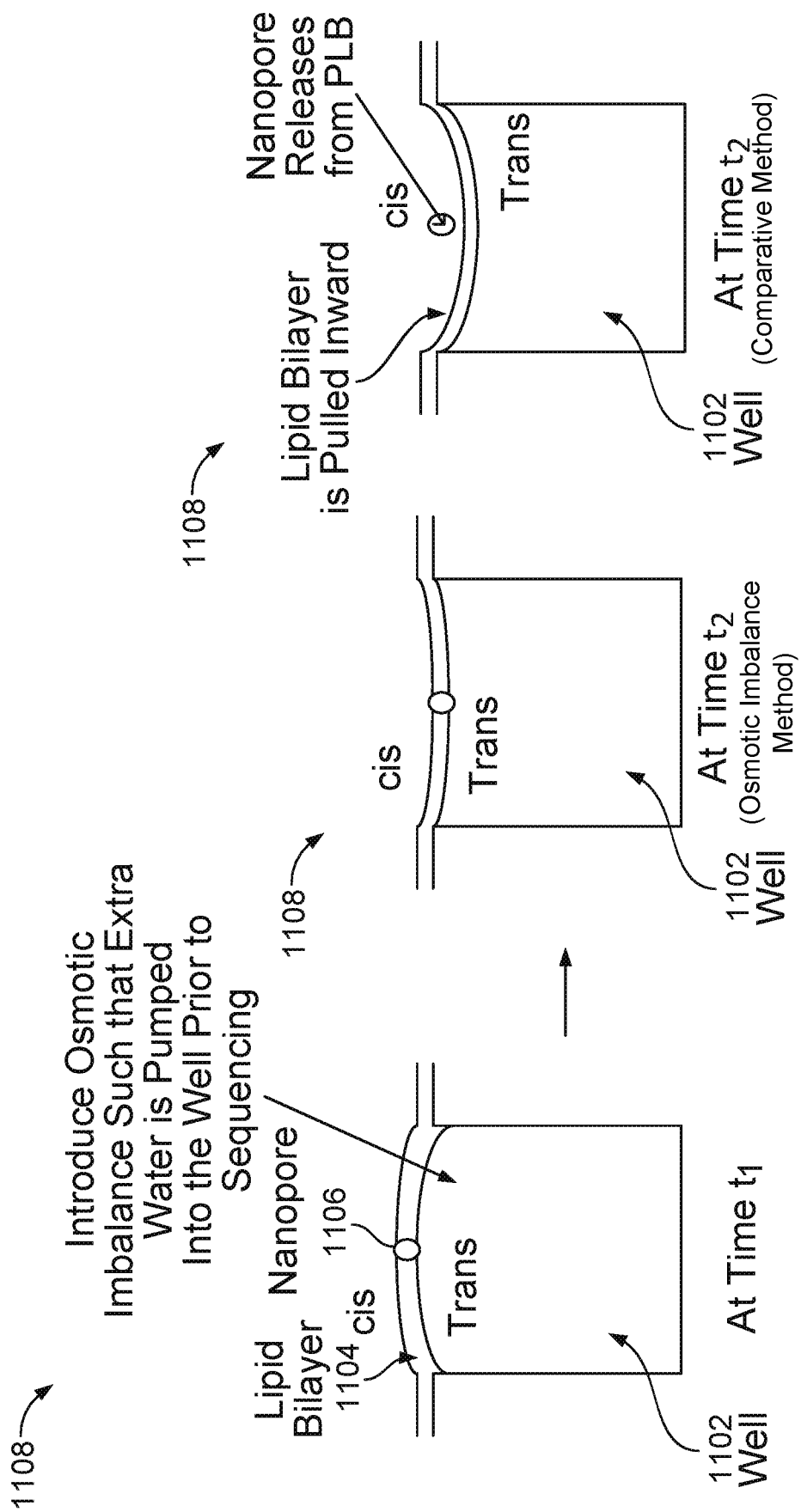

COUNTERACTING OSMOTIC IMBALANCE IN A SEQUENCING CELL

CROSS-REFERENCE TO RELATED APPLICATION

This application claims priority to U.S. Provisional Application No. 62/355,114, filed Jun. 27, 2016, the disclosure of which is hereby incorporated by reference in its entirety for all purposes.

BACKGROUND

Nanopore sequencing systems generally use a protein pore in a planar lipid bilayer (PLB) suspended over a well (e.g., a cylindrical well) containing an electrolyte solution, which is also present in a much larger exterior reservoir (e.g., above the well). A working electrode and counter electrode are used to apply an electrical bias across the well and the exterior reservoir. The PLB extends over the well to both electrically and physically seal the well, and the PLB separates the well from the larger exterior reservoir. While neutral molecules, such as water and dissolved gases, may pass through the PLB, ions may not. A protein pore in the PLB provides a path for ions to be conducted into and out of the well.

Protein pores such as alpha hemolysin (aHL) are known to preferentially conduct either anions or cations and to have unequal conductivity under positive and negative electrical bias (Noskov et al., (2004) Biophys J. 87:2299). Such properties may lead to a net influx from or efflux into the well, which leads to diffusion of water through the PLB to balance the electrolyte concentration between the well and the external reservoir. Such diffusion can cause instability.

BRIEF SUMMARY

One provided method of analyzing a molecule includes forming a lipid bilayer that divides a first reservoir from a second reservoir. The first reservoir has a first reservoir osmolarity, and the second reservoir has a second reservoir osmolarity. The method further includes flowing an electrolyte solution to the first reservoir, wherein the electrolyte solution has an electrolyte solution osmolarity that differs from the first reservoir osmolarity, thereby making a first change to a ratio of the first reservoir osmolarity to the second reservoir osmolarity. The method further includes applying a voltage across the lipid bilayer, wherein the lipid bilayer includes a nanopore, and wherein the voltage causes a net transfer of ions between the first reservoir and the second reservoir, thereby making a second change to the ratio of the first reservoir osmolarity to the second reservoir osmolarity. The first change to the ratio and the second change to the ratio substantially counterbalance each other.

In some embodiments, the net transfer of ions between the first reservoir and the second reservoir includes a net efflux of ions from the second reservoir to the first reservoir. In some embodiments, the net efflux of ions from the second reservoir to the first reservoir increases the ratio of the first reservoir osmolarity to the second reservoir osmolarity, and flowing the electrolyte solution to the first reservoir decreases the ratio of the first reservoir osmolarity to the second reservoir osmolarity. In some embodiments, the electrolyte solution osmolarity is lower than the second reservoir osmolarity before the electrolyte solution is flowed to the first reservoir. In some embodiments, the method further includes progressively reducing the electrolyte solution osmolarity from an initial electrolyte solution osmolarity to a final electrolyte solution osmolarity to make the first change to the ratio of the first reservoir osmolarity to the second reservoir osmolarity.

In some embodiments, the net transfer of ions between the first reservoir and the second reservoir includes a net influx of ions into the second reservoir from the first reservoir. In some embodiments, the net influx of ions into the second reservoir from the first reservoir decreases the ratio of the first reservoir osmolarity to the second reservoir osmolarity, and flowing the electrolyte solution to the first reservoir increases the ratio of the first reservoir osmolarity to the second reservoir osmolarity. In some embodiments, the electrolyte solution osmolarity is higher than the second reservoir osmolarity before the electrolyte solution is flowed to the first reservoir. In some embodiments, the method further includes progressively increasing the electrolyte solution osmolarity from an initial electrolyte solution osmolarity to a final electrolyte solution osmolarity to make the first change to the ratio of the first reservoir osmolarity to the second reservoir osmolarity.

In some embodiments, the method further includes inserting the nanopore into the lipid bilayer before the electrolyte solution is flowed to the first reservoir. In some embodiments, the method further includes inserting the nanopore into the lipid bilayer after the electrolyte solution is flowed to the first reservoir. In some embodiments, the lipid bilayer spans across the second reservoir, and the first reservoir is external to the second reservoir. In some embodiments, the first reservoir has a first reservoir volume, the second reservoir has a second reservoir volume, and the first reservoir volume is larger than the second reservoir volume. In some embodiments, the voltage applied across the lipid bilayer is an alternating current voltage. In some embodiments, the voltage applied across the lipid bilayer is a direct current voltage.

Also provided is a system for analyzing molecules in a sequencing chip, the system including a sequencing chip including an array of cells, wherein each of the cells includes a well. The system further includes a reservoir coupled to the sequencing chip. The system further includes a processor or a circuitry configured to form a lipid bilayer that divides the reservoir from the well of one of the array of cells. The reservoir has a first reservoir osmolarity, and the well has a second reservoir osmolarity. The processor or circuitry is further configured to flow an electrolyte solution to the reservoir, wherein the electrolyte solution has an electrolyte solution osmolarity that differs from the first reservoir osmolarity, thereby making a first change to a ratio of the first reservoir osmolarity to the second reservoir osmolarity. The processor or circuitry is further configured to apply a voltage across the lipid bilayer, wherein the lipid bilayer includes a nanopore, and wherein the voltage causes a net transfer of ions between the reservoir and the well, thereby making a second change to the ratio of the first reservoir osmolarity to the second reservoir osmolarity. The first change to the ratio and the second change to the ratio substantially counterbalance each other.

In some embodiments, the net transfer of ions between the reservoir and the well includes a net efflux of ions from the well to the reservoir. In some embodiments, the net efflux of ions from the well to the reservoir increases the ratio of the first reservoir osmolarity to the second reservoir osmolarity, and flowing the electrolyte solution to the reservoir decreases the ratio of the first reservoir osmolarity to the second reservoir osmolarity. In some embodiments, the electrolyte solution osmolarity is lower than the second reservoir osmolarity before the electrolyte solution is flowed to the reservoir. In some embodiments, the method further includes progressively reducing the electrolyte solution osmolarity from an initial electrolyte solution osmolarity to a final electrolyte solution osmolarity to make the first change to the ratio of the first reservoir osmolarity to the second reservoir osmolarity.

In some embodiments, the net transfer of ions between the reservoir and the well comprises a net influx of ions into the well from the reservoir. In some embodiments, the net influx of ions into the well from the reservoir decreases the ratio of the first reservoir osmolarity to the second reservoir osmolarity, and flowing the electrolyte solution to the reservoir increases the ratio of the first reservoir osmolarity to the second reservoir osmolarity. In some embodiments, the electrolyte solution osmolarity is higher than the second reservoir osmolarity before the electrolyte solution is flowed to the reservoir. In some embodiments, the method further includes progressively increasing the electrolyte solution osmolarity from an initial electrolyte solution osmolarity to a final electrolyte solution osmolarity to make the first change to the ratio of the first reservoir osmolarity to the second reservoir osmolarity y.

In some embodiments, the processor or the circuitry is further configured to insert the nanopore into the lipid bilayer before the electrolyte solution is flowed to the reservoir. In some embodiments, the processor or the circuitry is further configured to insert the nanopore into the lipid bilayer after the electrolyte solution is flowed to the reservoir. In some embodiments, the lipid bilayer spans across the well, and the reservoir is external to the well. In some embodiments, the reservoir has a reservoir volume, the well has a well volume, and the reservoir volume is larger than the well volume. In some embodiments, the voltage applied across the lipid bilayer is an alternating current voltage. In some embodiments, the voltage applied across the lipid bilayer is a direct current voltage.

A better understanding of the nature and advantages of embodiments of the present invention may be gained with reference to the following detailed description and the accompanying drawings.

BRIEF DESCRIPTION OF THE DRAWINGS

FIG. 11A illustrates that by flowing over a lipid bilayer a lower concentration of electrolyte solution than is initially present in the well while the planar lipid bilayer is in place between the well and the external reservoir, excess water is forced into the well, causing the planar lipid bilayer to bow upwards.

FIG. 11B illustrate that at time $t_2$ the excess volume of water that was previously forced into the well due to the initial flow of lower concentration electrolyte allows for a greater volume of water to be removed from the well before the planar lipid bilayer ruptures FIG. 11C illustrate that at time $t_2$ for a comparative method, volume of water removed from the well forces the nanopore to exit the planar lipid bilayer.

TERMS

Figure 1:
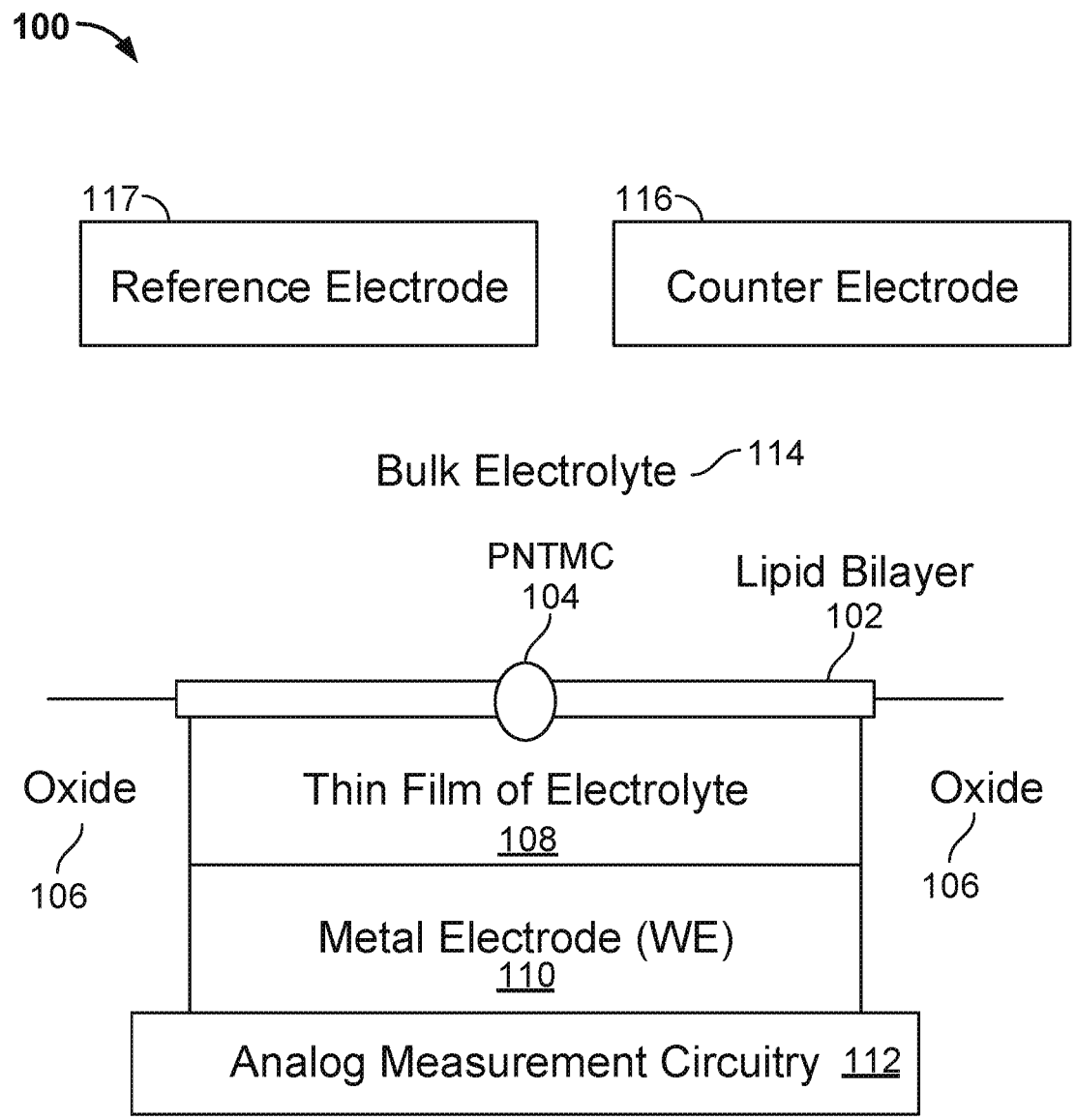
FIG. 1 illustrates an embodiment of a cell 100 in a nanopore based sequencing chip.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

"Nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. Some nanopores are proteins.

"Osmolarity", also known as osmotic concentration, refers to a measure of solute concentration. Osmolarity measures the number of osmoles of solute particles per unit volume of solution. An osmole is a measure of the number of moles of solute that contribute to the osmotic pressure of a solution. Osmolarity allows the measurement of the osmotic pressure of a solution and the determination of how the solvent will diffuse across a semipermeable membrane (osmosis) separating two solutions of different osmotic concentration.

"Osmolyte" as used herein refers to any soluble compound that when dissolved into a solution increases the osmolarity of that solution.

"Polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus*, *Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ∈, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

"Nucleic acid" can refer to deoxyribonucleotides or ribonucleotides and polymers thereof in either single- or double-stranded form. The term can encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs can include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

"Template" refers to a strand of a nucleic acid from which a complementary nucleic acid strand is synthesized by a DNA polymerase, for example, in a primer extension reaction.

"Nucleotide," in addition to referring to the naturally occurring ribonucleotide or deoxyribonucleotide monomers, can be understood to refer to related structural variants thereof, including derivatives and analogs, that are functionally equivalent with respect to the particular context in which the nucleotide is being used (e.g., hybridization to a complementary base), unless the context clearly indicates otherwise.

"Tag" refers to a detectable moiety that can be atoms or molecules, or a collection of atoms or molecules. A tag can provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag can be attached to the nucleotide via the phosphate moiety.

"Substantially counterbalance" as used herein refers to a relationship between two or more changes to an initial value or state, the net effect of which is a change to a value or state that differs from the initial value or state by 60% or less. The initial value can be, for example, the ratio of the osmolarity values of two different solutions, or the volume of liquid within a reservoir. Two changes to the initial value can be considered to substantially counterbalance each other if the net effect of the changes results in a new value (i.e., a new ratio of osmolarity values) that is 60% less than, 55% less than, 50% less than, 45% less than, 40% less than, 35% less than, 30% less than, 25% less than, 20% less than, 18% less than, 16% less than, 14% less than, 12% less than, 10% less than, 8% less than, 6% less than, 4% less than, 2% less than, identical to, 2% greater than, 4% greater than, 6% greater than, 8% greater than, 10% greater than, 12% greater than, 14% greater than, 16% greater than, 18% greater than, 20% greater than, 25% greater than, 30% greater than, 35% greater than, 40% greater than, 45% greater than, 50% greater than, 55% greater than, or 60% greater than the initial value. As another example, two changes can substantially counterbalance one another if the value of the differences between the two changes, divided by the value of either the first or second change, is less than 60%.

Alternatively, two changes to an initial value or state can be considered to substantially counterbalance one another if the larger of the two changes has a magnitude that is no greater than 60% larger than the magnitude of the smaller of the two changes. For example, the larger change can have a magnitude that is no more than 160% of, no more than 150% of, no more than 140% of, no more than 130% of, no more than 120% of, no more than 110% of, no more than 108% of, no more than 106%, no more than 104% of, or no more than 102% of the magnitude of the smaller change.

DETAILED DESCRIPTION

Techniques disclosed herein relate to nanopore-based DNA sequencing, and more specifically, to the use of osmotic imbalance to increase the stability and longevity of nanopores in sequencing cells. Embodiments can utilize osmolarity imbalance to modulate the time at which a bilayer enters a state that either causes pore ejection or bilayer failure. In this manner, embodiments can delay (or prevent premature) pore ejection or bilayer failure. Such techniques can help maintain a more constant volume on either side (cis and trans side) of a lipid bilayer containing a nanopore.

Example nanopore systems, circuitry, and sequencing operations are initially described, followed by example techniques to increase the useful lifespan of nanopores in DNA sequencing cells. The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor.

I. Nanopore System

A. Nanopore Sequencing Cell

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions through the nanopore can be observed. The size of the current is sensitive to the pore size.

A nanopore based sequencing chip may be used for nucleic acid (e.g., DNA) sequencing. A nanopore based sequencing chip incorporates a large number of sensor cells configured as an array. For example, an array of one million cells can include 1000 rows by 1000 columns of cells.

FIG. 1 illustrates an embodiment of a cell 100 in an array of cells that form a nanopore based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest (e.g., a single polymer molecule, such as DNA) can be placed directly onto the surface of the cell. A single PNTMC 104 can be inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 can modulate the ionic current through the otherwise impermeable bilayer.

Analog measurement circuitry 112 is connected to a working electrode 110 (e.g., made of metal) covered by a volume of electrolyte 108 inside a well formed in an oxide layer 106. The volume of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116. The cell can also include a reference electrode 117, which can act as an electrochemical potential sensor.

Figure 5:
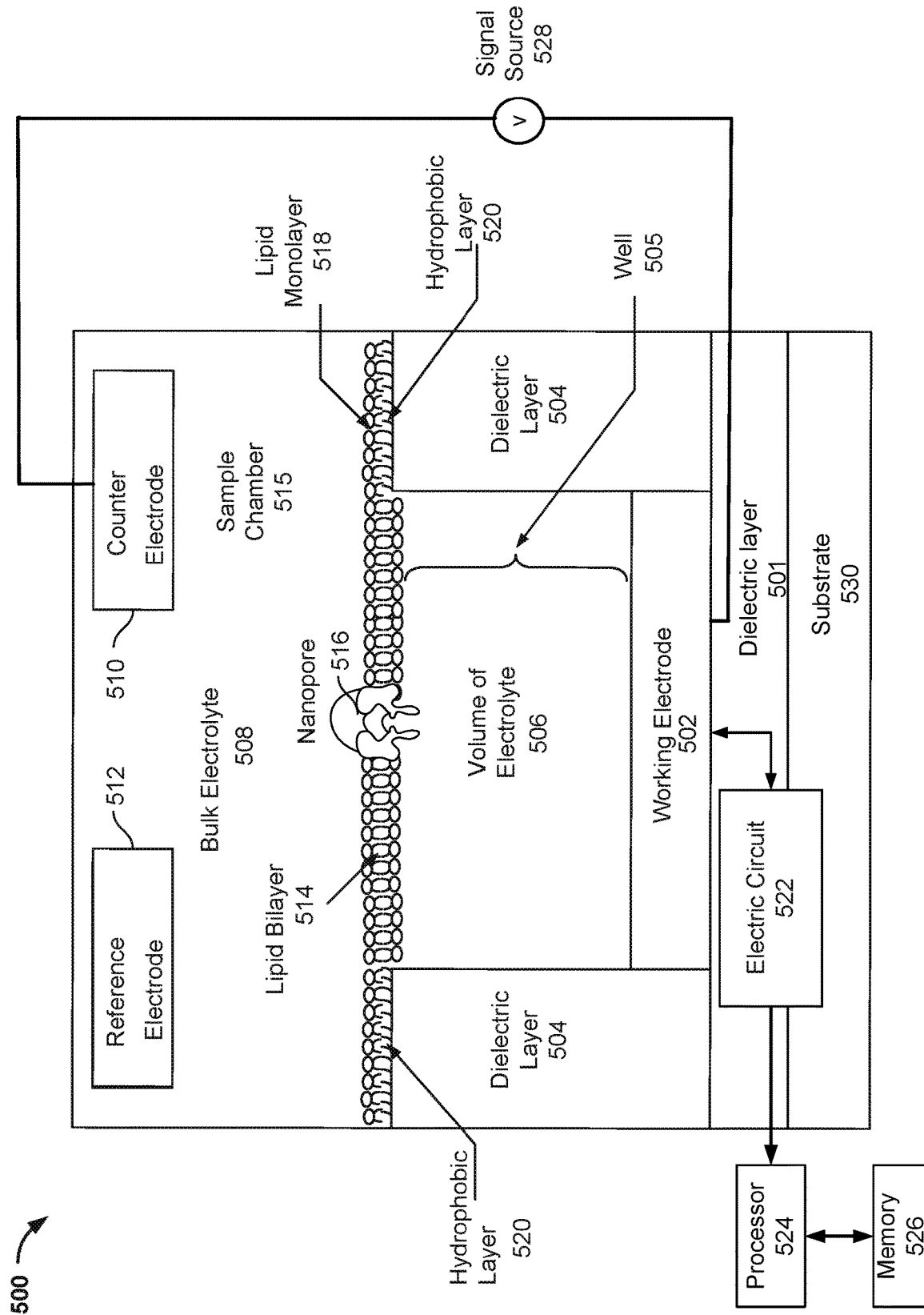
FIG. 5 illustrates an embodiment of a cell 500 in a nanopore based sequencing chip.

FIG. 5 illustrates an embodiment of a cell 500 in a nanopore based sequencing chip. Cell 500 includes a well 505 having two side walls and a bottom. In one embodiment, each side wall comprises a dielectric layer 504 and the bottom comprises a working electrode 502. In one embodiment, the working electrode 502 has a top side and a bottom side. In another embodiment, the top side of 502 makes up the bottom of the well 505 while the bottom side of 502 is in contact with dielectric layer 501. In another embodiment, the dielectric layer 504 is above dielectric layer 501. Dielectric layer 504 forms the walls surrounding a well 505 in which a working electrode 502 is located at the bottom. Suitable dielectric materials for use in the present invention (e.g., dielectric layer 501 or 504) include, without limitation, porcelain (ceramic), glass, mica, plastics, oxides, nitrides (e.g., silicon mononitride or SiN), silicon oxynitride, metal oxides, metal nitrides, metal silicates, transition-metal oxides, transition-metal nitrides, transition metal-silicates, oxynitrides of metals, metal aluminates, zirconium silicate, zirconium aluminate, hafnium oxide, insulating materials (e.g., polymers, epoxies, photoresist, and the like), or combinations thereof. Those of ordinary skill in the art will appreciate other dielectric materials that are suitable for use in the present invention.

As shown in FIG. 5, nanopore cell 500 can be formed on a substrate 530, such as a silicon substrate. Dielectric layer 501 may be formed on substrate 530. Dielectric material used to form dielectric layer 501 may include, for example, glass, oxides, nitrides, and the like. An electric circuit 522 for controlling electrical stimulation and for processing the signal detected from nanopore cell 500 can be formed on substrate 530 and/or within dielectric layer 501. For example, a plurality of patterned metal layers (e.g., metal 1 to metal 6) can be formed in dielectric layer 501, and a plurality of active devices (e.g., transistors) can be fabricated on substrate 530. In some embodiments, signal source 528 is included as a part of electric circuit 522. Electric circuit 522 can include, for example, amplifiers, integrators, analog-to-digital converters, noise filters, feedback control logic, and/or various other components. Electric circuit 522 can be further coupled to a processor 524 that is coupled to a memory 526, where processor 524 can analyze the sequencing data to determine sequences of the polymer molecules that have been sequenced in the array.

In one aspect, cell 500 also includes one or more hydrophobic layers. As shown in FIG. 5, each dielectric layer 504 has a top surface. In one embodiment, the top surface of each dielectric layer 504 may comprise a hydrophobic layer. In one embodiment, silanization forms a hydrophobic layer 520 above the top surface of dielectric layer 504. For example, further silanization with silane molecules that are (i) containing 6 to 20 carbon-long chains (e.g., octadecyl-trichlorosilane, octadecyl-trimethoxysilane, or octadecyl-triethoxysilane), (ii) dimethyloctylchlorosilane (DMOC), or (iii) organofunctional alkoxysilane molecules (e.g., dimethylchloro-octadecyl-silane, methyldichloro-octadecyl-silane, trichloro-octadecyl-silane, trimethyl-octadecyl-silane, or triethyl-octadecyl-silane) can be done on the top surface of dielectric layer 504. In one embodiment, the hydrophobic layer is a silanized layer or silane layer. In one embodiment, the silane layer can be one molecule in thickness. In one aspect, dielectric layer 504 comprises a top surface suitable for adhesion of a membrane (e.g., a lipid bilayer comprising a nanopore). In one embodiment, the top surface suitable for adhesion of a membrane comprises a silane molecule as described herein. Alternatively, the hydrophobic layer can be a polyimide layer, which is also a dielectric. Polyimide materials have thermal stability, good chemical resistance, and excellent mechanical properties. In some embodiments, hydrophobic layer 520 has a thickness provided in a nanometer (nM) or micrometer (μm) scale. In other embodiments, the hydrophobic layer may extend down along all or a part of the dielectric layer 504 (see also Davis et al. U.S. 20140034497, which is incorporated herein by reference in its entirety).

In another aspect, well 505 (formed by the dielectric layer walls 504) further includes a volume of salt solution 506 above working electrode 502. In general, the methods of the present invention comprise the use of a solution (e.g., a salt solution, salt buffer solution, electrolyte, electrolyte solution, or bulk electrolyte) that comprises osmolytes. In the present invention, an osmolyte is a compound that is soluble in solution within the architecture of a nanopore sequencing system, e.g., a well containing a salt solution or a bulk electrolyte as described herein. As such, the osmolytes of the present invention affect osmosis, particularly osmosis across a lipid bilayer. Osmolytes for use in the present invention include, without limitation, ionic salts such as lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$); polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, alpha-alanine, arginine, proline, taurine, betaine, octopine, glutamate, sarcosine, y-aminobutyric acid, and trimethylamine N-oxide ("TMAO") (see also e.g., Fisher et al. U.S. 20110053795, incorporated herein by reference in its entirety). In one embodiment, the present invention utilizes a solution comprising an osmolyte, wherein the osmolyte is an ionic salt. Those of ordinary skill in the art will appreciate other compounds that are suitable osmolytes for use in the present invention. In another aspect, the present invention provides solutions comprising two or more different osmolytes. In some embodiments, the film of salt solution 506 has a thickness of about three microns (μm).

The architecture of the nanopore based sequencing chip described herein comprises an array of wells (e.g., FIG. 5) having various volume capacities, including nanoliter (nL), picoliter (pL), femtoliter (fL), attoliter (aL), zeptoliter (zL) and yocoliter (yL) capacities. For example, the volume of electrolyte 108 (e.g., FIG. 1) or salt solution 506 (e.g., FIG. 5) is provided in a nL, pL, fL, aL, zL, or yL scale. In one embodiment of the present invention, the volume of the electrolyte or salt solution formed by the wells (e.g., well 505 in FIG. 5) of the present invention, or the volume of electrolyte or salt solution used in methods described herein may be provided in a nanoliter (nL), picoliter (pL), femtoliter (fL), attoliter (aL), zeptoliter (zL), or yocoliter (yL) scale. The wells may alternately be described by their volume in cubic micrometers, or similar dimensions, rather than by volume. It will be within the ability of one skilled in the art to determine the necessary conversion between units, for example from cubic micrometers to picoliters, femtoliters, or the like.

As shown in FIG. 5, a membrane is formed on the top surfaces of dielectric layer 504 and spans across well 505. For example, the membrane includes a lipid monolayer 518 formed on top of hydrophobic layer 520. As the membrane reaches the opening of well 505, the lipid monolayer transitions to a lipid bilayer 514 that spans across the opening of the well. The lipid monolayer 518 may also extend along all or a part of the vertical surface (i.e., side wall) of a dielectric layer 504. In one embodiment, the vertical surface 504 along which the monolayer 518 extends comprises a hydrophobic layer. A bulk electrolyte 508 containing protein nanopore transmembrane molecular complexes (PNTMC) and the analyte of interest is placed directly above the well. A single PNTMC/nanopore 516 is inserted into lipid bilayer 514. In one embodiment, insertion into the bilayer is by electroporation. Nanopore 516 crosses lipid bilayer 514 and provides the only path for ionic flow from bulk electrolyte 508 to working electrode 502. Bulk electrolyte 508 can further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$).

Cell 500 includes a counter electrode (CE) 510, which is in electrical contact with the bulk electrolyte 508. Cell 500 may optionally include a reference electrode 512. In some embodiments, counter electrode 510 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 502 is a metal electrode. For non-faradaic conduction, working electrode 502 may be made of metals that are resistant to corrosion and oxidation, e.g., platinum, gold, titanium nitride and graphite. For example, working electrode 502 may be a platinum electrode with electroplated platinum. In another example, working electrode 502 may be a titanium nitride (TiN) working electrode.

As shown in FIG. 5, nanopore 516 is inserted into the planar lipid bilayer 514 suspended over well 505. An electrolyte solution is present both inside well 505, i.e., trans side, (see salt solution 506) and in a potentially much larger external reservoir 522, i.e., cis side, (see bulk electrolyte 508). The bulk electrolyte 508 in external reservoir 522 can be above multiple wells of the nanopore based sequencing chip. Lipid bilayer 514 extends over well 505 and transitions to lipid monolayer 518 where the monolayer is attached to hydrophobic layer 520.

This geometry both electrically and physically seals well 505 and separates the well from the larger external reservoir. While neutral molecules, such as water and dissolved gases, can pass through lipid bilayer 514, ions cannot. Nanopore 516 in lipid bilayer 514 provides a single path for ions to be conducted into and out of well 505.

For nucleic acid sequencing, a polymerase is attached to nanopore 516. A template of DNA is held by the polymerase. The polymerase synthesizes DNA by incorporating hexaphosphate mono-nucleotides (HMN) from solution that are complementary to the template. A unique, polymeric tag is attached to each HMN. During incorporation, the tag threads the nanopore aided by an electric field gradient produced by the voltage between counter electrode 510 and working electrode 502. The tag partially blocks nanopore 516, procuring a measurable change in the ionic current through nanopore 516. In some embodiments, an alternating current (AC) bias or direct current (DC) voltage is applied between the electrodes.

B. Nanopore-Based Sequencing by Synthesis

Figure 2:
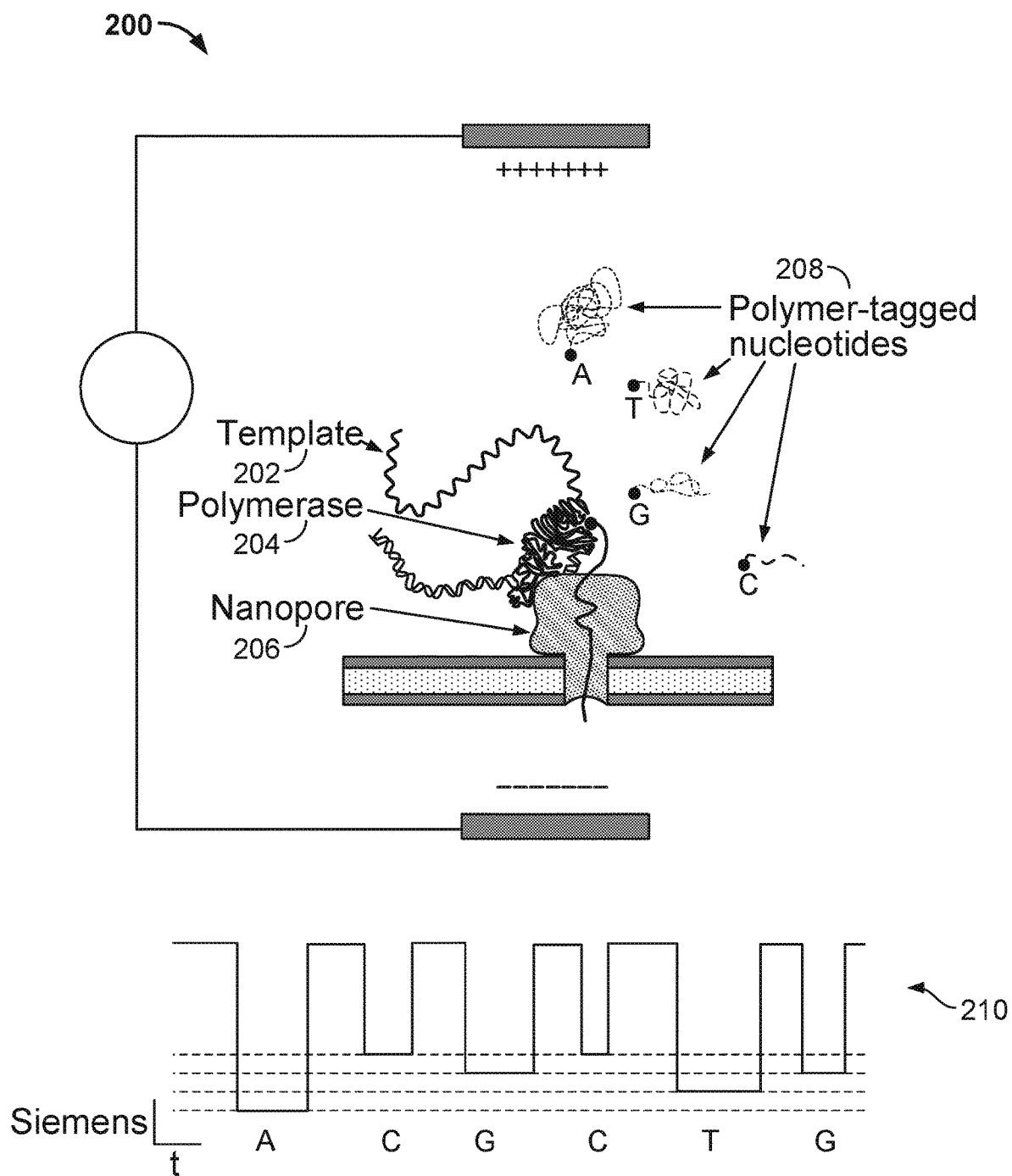
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
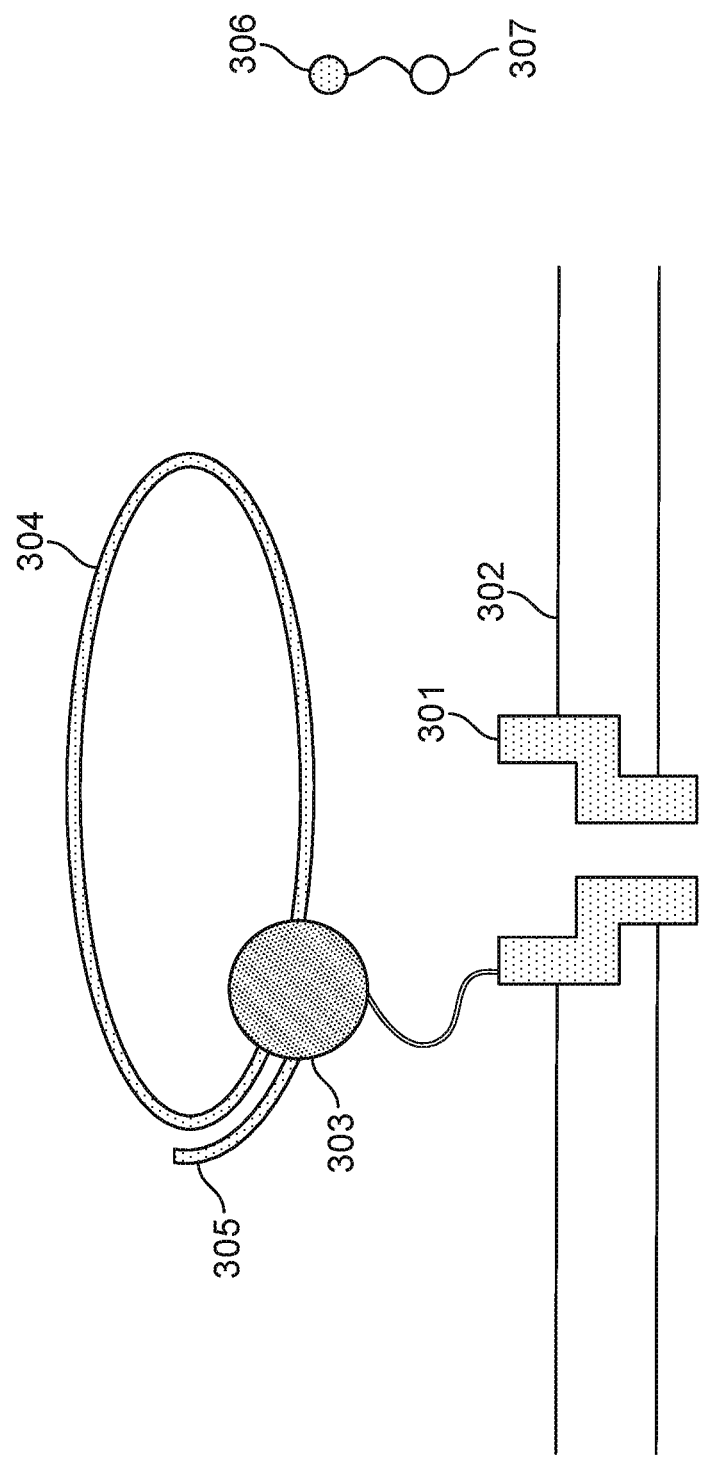
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
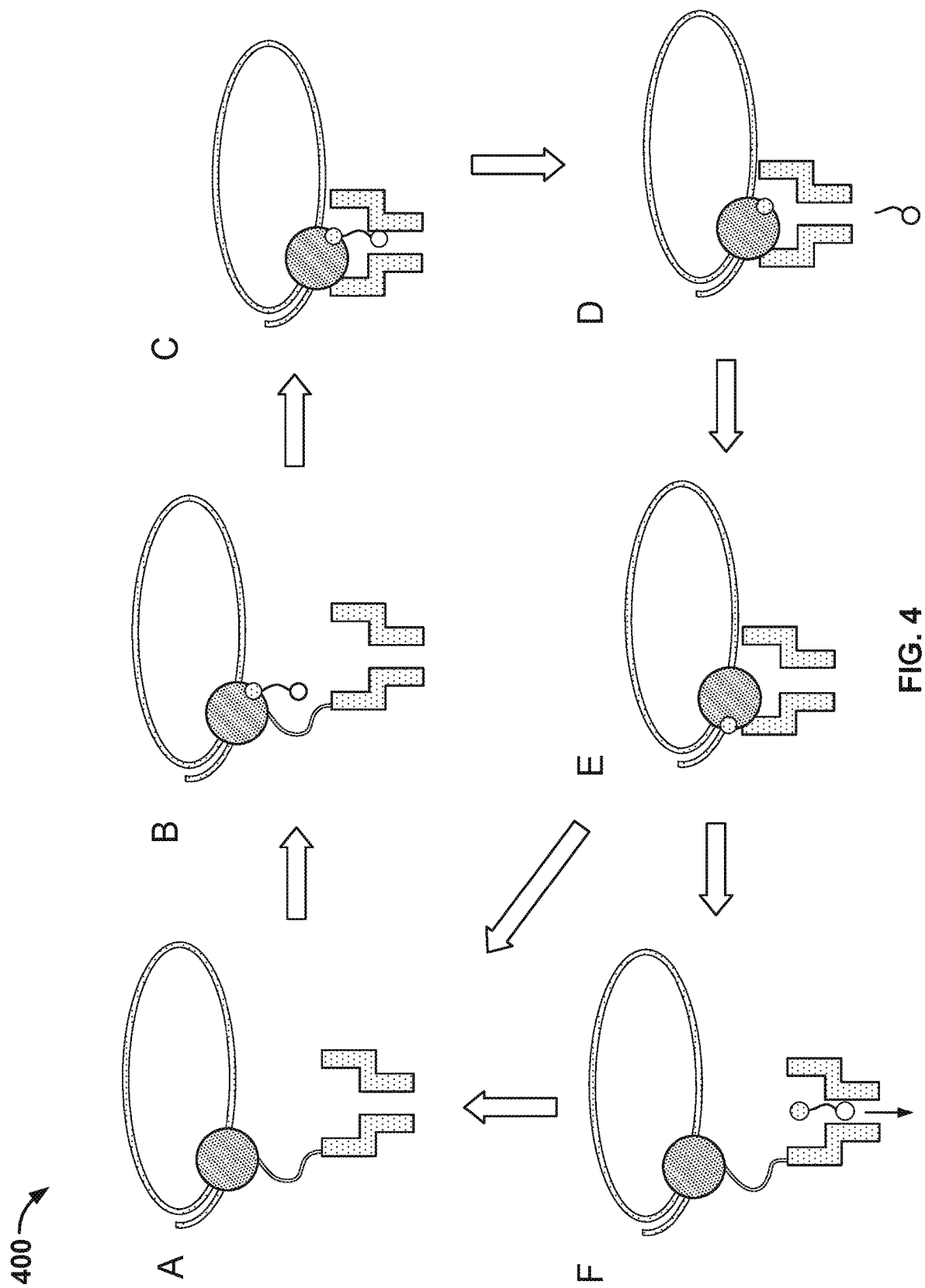
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10,000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

In various embodiments, before the polymerase is docked to the nanopore, the conductance of the nanopore is ~300 picosiemens (300 pS). At stage C, the conductance of the nanopore is about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Further details regarding the nanopore-based sequencing can be found in, for example, U.S. patent application Ser. No. 14/577,511 entitled "Nanopore-Based Sequencing With Varying Voltage Stimulus," U.S. patent application Ser. No. 14/971,667 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation."

II. Measurement Circuitry

Figure 13A:
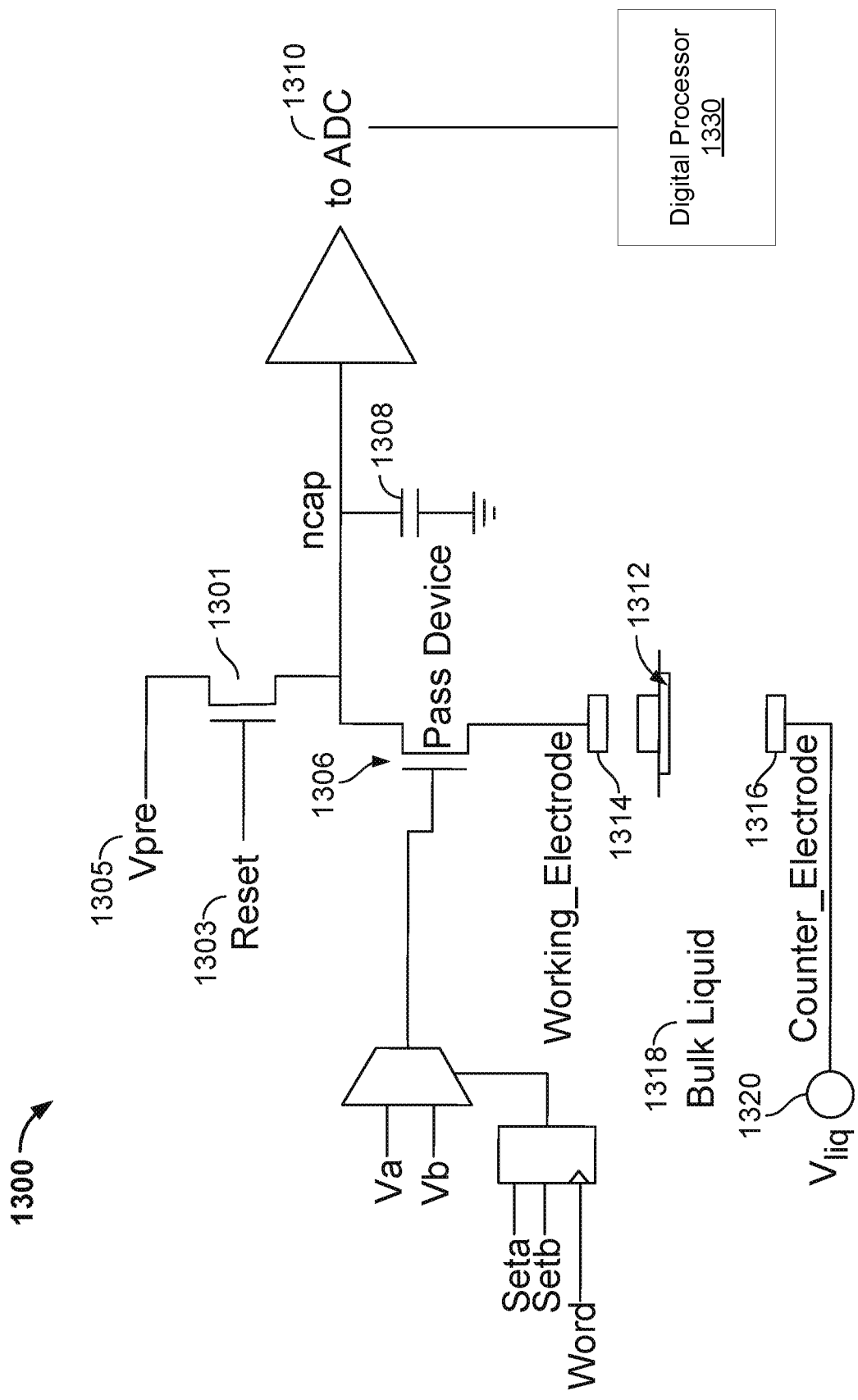
FIG. 13A illustrates an embodiment of a circuitry 1300 in a cell of a nanopore based sequencing chip, wherein the circuitry can be configured to detect whether a lipid bilayer is formed in the cell without causing an already formed lipid bilayer to break down.

FIG. 13A shows a lipid membrane or lipid bilayer 1312 situated between a cell working electrode 1314 and a counter electrode 1316, such that a voltage is applied across lipid membrane/bilayer 1312. A lipid bilayer is a thin membrane made of two layers of lipid molecules. A lipid membrane is a membrane having a thickness of several molecules (more than two) of lipid molecules. Lipid membrane/bilayer 1312 is also in contact with a bulk liquid/electrolyte 1318. Note that working electrode 1314, lipid membrane/bilayer 1312, and counter electrode 1316 are drawn upside down as compared to the working electrode, lipid bilayer, and counter electrode in FIG. 1. In some embodiments, the counter electrode is shared between a plurality of cells, and is therefore also referred to as a common electrode. The common electrode can be configured to apply a common potential to the bulk liquid in contact with the lipid membranes/bilayers in the measurements cells by connecting the common electrode to a voltage source $V_{liq}$ 1320. The common potential and the common electrode are common to all of the measurement cells. There is a working cell electrode within each measurement cell; in contrast to the common electrode, working cell electrode 1314 is configurable to apply a distinct potential that is independent from the working cell electrodes in other measurement cells.

Figure 13B:
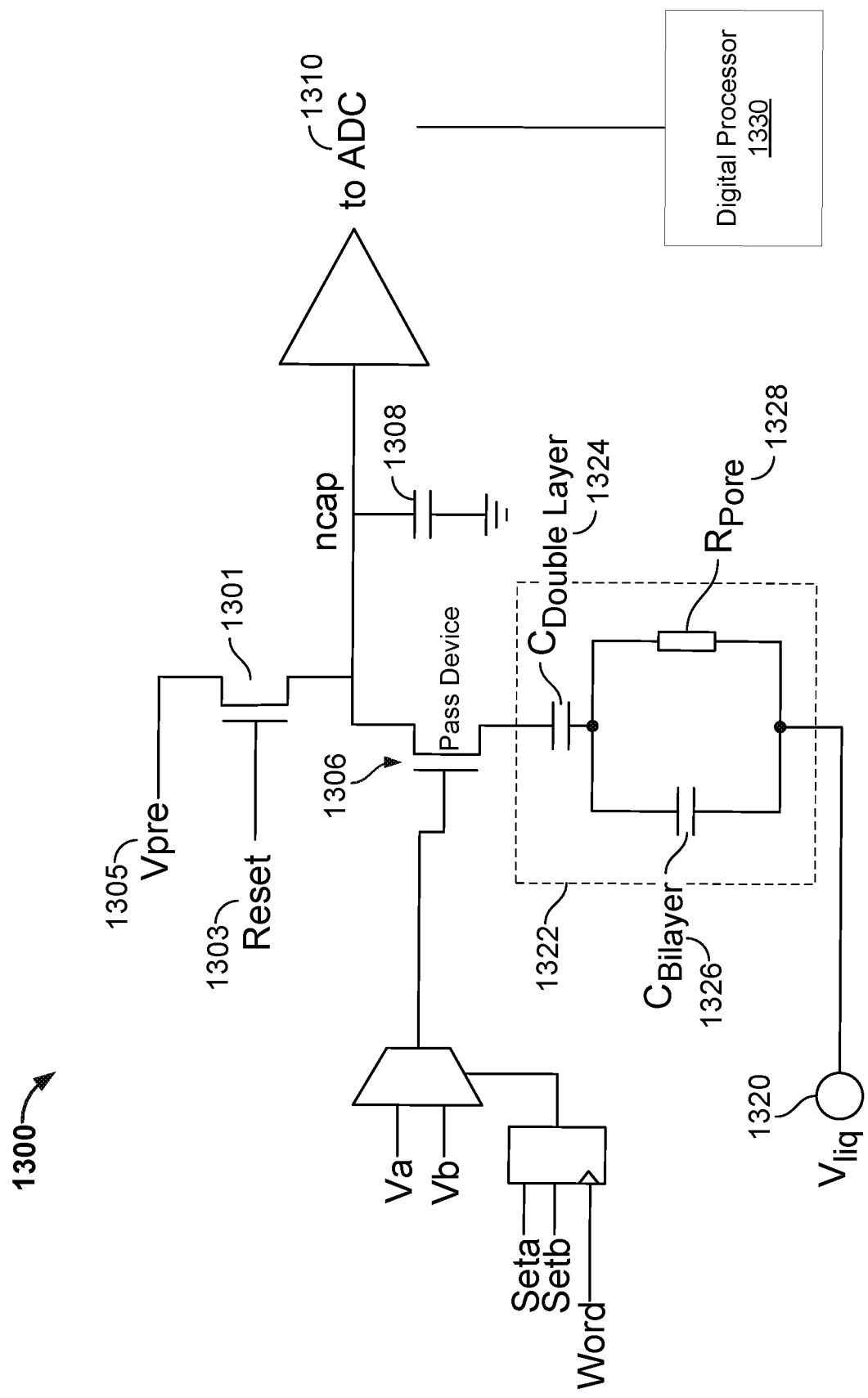
FIG. 13B illustrates the same circuitry 1300 in a cell of a nanopore based sequencing chip as that shown in FIG. 13A. Comparing to FIG. 13A, instead of showing a lipid membrane/bilayer between the working electrode and the counter electrode, an electrical model representing the electrical properties of the working electrode and the lipid membrane/bilayer is shown.

FIG. 13B illustrates the same circuitry 1300 in a cell of a nanopore based sequencing chip as that shown in FIG. 13A. Comparing to FIG. 13A, instead of showing a lipid membrane/bilayer between the working electrode and the counter electrode, an electrical model representing the electrical properties of the working electrode and the lipid membrane/bilayer is shown.

Electrical model 1322 includes a capacitor 1324 representing the electrical properties of working electrode 1314. The capacitance associated with working electrode 1314 is also referred to as a double layer capacitance ($C_{double\ layer}$). Electrical model 1322 further includes a capacitor 1326 ($C_{bilayer}$) that models a capacitance associated with the lipid membrane/bilayer and a resistor 1328 ($R_{pore}$ 1 that models a resistance associated with the nanopore, which can change based on the presence a particular tag in the nanopore.

Voltage source $V_{liq}$ 1320 is an alternating current (AC) voltage source. Counter electrode 1316 is immersed in the bulk liquid 1318, and an AC non-Faradaic mode is utilized to modulate a square wave voltage $V_{liq}$ and apply it to the bulk liquid in contact with the lipid membranes/bilayers in the measurement cells. In some embodiments, $V_{liq}$ is a square wave with a magnitude of ±200-250 mV and a frequency between 25 and 100 Hz.

Pass device 1306 is a switch that can be used to connect or disconnect the lipid membrane/bilayer and the electrodes from the measurement circuitry 1300. The switch enables or disables a voltage stimulus that can be applied across the lipid membrane/bilayer in the cell. Before lipids are deposited to the cell to form a lipid bilayer, the impedance between the two electrodes is very low because the well of the cell is not sealed, and therefore switch 1306 is kept open to avoid a short-circuit condition. Switch 1306 may be closed once lipid solvent has been deposited to the cell that seals the well of the cell.

Circuitry 1300 further includes an on-chip fabricated integrating capacitor 1308 ($n_{cap}$). Integrating capacitor 1308 is pre-charged by using a reset signal 1303 to close switch 1301, such that integrating capacitor 1308 is connected to a voltage source $V_{pre}$ 1305. In some embodiments, voltage source $V_{pre}$ 1305 provides a constant positive voltage with a magnitude of 900 mV. When switch 1301 is closed, integrating capacitor 1308 is pre-charged to the positive voltage level of voltage source $V_{pre}$ 1305.

After integrating capacitor 1308 is pre-charged, reset signal 1303 is used to open switch 1301 such that integrating capacitor 1308 is disconnected from voltage source $V_{pre}$ 1305. At this point, depending on the level of $V_{liq}$, the potential of counter electrode 1316 may be at a higher level than the potential of working electrode 1314, or vice versa. For example, during the positive phase of square wave $V_{liq}$ (i.e., the dark period of the AC voltage source signal cycle), the potential of counter electrode 1316 is at a higher level than the potential of working electrode 1314. Similarly, during the negative phase of square wave $V_{liq}$ (i.e., the bright period of the AC voltage source signal cycle), the potential of counter electrode 1316 is at a lower level than the potential of working electrode 1314. Due to this potential difference, integrating capacitor 1308 may be charged during the bright period of the AC voltage source signal cycle and discharged during the dark period of the AC voltage source signal cycle.

Depending on the sampling rate of an analog-to-digital converter (ADC) 1310, integrating capacitor 1308 charges or discharges for a fixed period of time, and then the voltage stored in integrating capacitor 1308 may be read out by ADC 1310. After the sampling by ADC 1310, integrating capacitor 1308 is pre-charged again by using reset signal 1303 to close switch 1301, such that integrating capacitor 1308 is connected to voltage source $V_{pre}$ 1305 again. In some embodiments, the sampling rate of ADC 1310 is between 1500 to 2000 Hz. In some embodiments, the sampling rate of ADC 1310 is up to 5 kHz. For example, with a sampling rate of 1 kHz, integrating capacitor 1308 charges or discharges for a period of ~1 ms, and then the voltage stored in integrating capacitor 1308 is read out by ADC 1310. After the sampling by ADC 1310, integrating capacitor 1308 is pre-charged again by using reset signal 1303 to close switch 1301 such that integrating capacitor 1308 is connected to voltage source $V_{pre}$ 1305 again. The steps of pre-charging the integrating capacitor 1308, waiting a fixed period of time for the integrating capacitor 1308 to charge or discharge, and sampling the voltage stored in integrating capacitor by ADC 1310 are then repeated in cycles throughout a lipid bilayer measurement phase of the system.

A digital processor 1330 can analyze the ADC values, e.g., for normalization. The digital processor can be implemented as hardware (e.g., in a GPU, FPGA, ASIC) or as a combination of hardware and software. In some embodiments, digital processor 1330 can perform further downstream processing.

Circuitry 1300 can be used to detect whether a lipid bilayer is formed in the cell by monitoring a delta voltage change, $\Delta V_{ADC}$, at integrating capacitor 1308 ($n_{cap}$) in response to a delta voltage change ($\Delta V_{liq}$) applied to the bulk liquid in contact with the lipid membrane/bilayer. During the lipid bilayer measurement phase, circuitry 1300 can be modeled as a voltage divider with $C_{bilayer}$ 1326, $C_{double\ layer}$ 1324, and $n_{cap}$ 1308 connected in series, and a voltage change tapped at an intermediate point of the voltage divider can be read by ADC 1310 for determining whether a lipid bilayer has been formed.

Further details regarding the measurement circuitry can be found in, for example, U.S. patent application Ser. No. 14/577,511 entitled "Nanopore-Based Sequencing With Varying Voltage Stimulus," U.S. patent application Ser. No. 14/971,667 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation."

III. Sequencing Operation

To perform sequencing, the value of the ADC (e.g., 1310) can be measured while a nucleotide is being added to a nucleic acid. The tag of the nucleotide can be pushed into the nanopore by the applied electric field across the nanopore, when the applied electric field is such that $V_{liq}$ is higher than $V_{pre}$.

A. Threading

A threading event in the context of a sequencing operation is when a tagged nucleotide is being attached to the DNA fragment, and the tag goes in and out of the well. This can happen multiple times during a threading event. When the tag is in the well, a lower ADC measurement of the current will occur.

During threading, some cycles (i.e., of AC cycle) will not have the tag in the well. The bright mode is the mode where a tag might be attracted into the well. A dark mode is when the tag is pushed out of the well. Open channel is when there is no tag in the well, and so the current is the highest (V=IR).

B. Bright and Dark Cycles

In some embodiments, an AC voltage is applied across the system, e.g., at 80 Hz. An acquisition rate of ADC can be about 1900 Hz. Thus, there can be about 23-24 data points (voltage measurements) taken per AC cycle (cycle of AC square wave). There are sets of points per AC cycle (i.e., sequencing cycle), where each set of points corresponds to one cycle of the AC waveform. In a set for an AC cycle, there is a subset for when $V_{liq}$ is higher than $V_{pre}$, which is called a bright mode (channel), as that is when the tag can be forced into the nanopore. Another set corresponds to a dark mode (channel) when the tag is pushed out of the nanopore by the applied electric field.

C. Decay within a Data Acquisition Cycle and Decrease in Measured Voltages within a Cycle For each set of data points, when the switch 1301 is opened, the voltage at $n_{cap}$ will change in a decaying manner, as an increase to $V_{liq}$ when $V_{liq}$ is higher than $V_{pre}$ or a decrease to $V_{liq}$ when $V_{liq}$ is lower than $V_{pre}$. The measured voltage can be at a predetermined time relative to when the switch 1301 opens. This voltage might be expected to be about the same for each measurement, but this is not the case when charge builds up as $C_{double\ layer}$ 1324. As a result, the voltage is shifted, thereby causing the measured value to decrease for each data point in a cycle. Thus, within a cycle the data point values will change somewhat from one data point to the next within a cycle to be closer to $V_{pre}$. The ΔADC value from $V_{pre}$ decreases from point to point within a cycle. A time constant of the system can be about 200-500 ms.

Accordingly, when the switch 1301 is opened and an ADC value is measured, each data point is a result of a decay for charging or discharging back to V. When the switch is closed, the ADC value is driven back to $V_{pre}$. The decays may not be measured fully, as only one data point is to be measured during each decay cycle, although high rates of measurement may be used. The decay is governed by the value of the resistance of the bilayer, which can include a nanopore, which can in turn include a molecule (e.g., tagged nucleotides).

The switch operates at the time of data acquisition. The switch would be closed for a relatively short time between two acquisitions of data. The switch would typically change right after measurement of the ADC. The switch allows multiple data points to be collected for each cycle. Otherwise, the value of the ADC would decay to $V_{liq}$, and stay there. Such multiple measurements can allow higher resolution with a fixed ADC (e.g., 8-bit to 14-bit due to the greater number of measurements, which may be averaged).

The multiple measurements also provide kinetic information, e.g., they can provide information about the molecule threads into the nanopore. The timing information allows for a determination of how long a threading event lasts. This can be used in helping to determine whether multiple nucleotides were added to the DNA strand being sequenced. Having the switch further allows for a voltage to be applied across the nanopore for longer periods of time, as otherwise the tag can move out of the nanopore, which again relates to only obtaining one data point.

Figure 14:
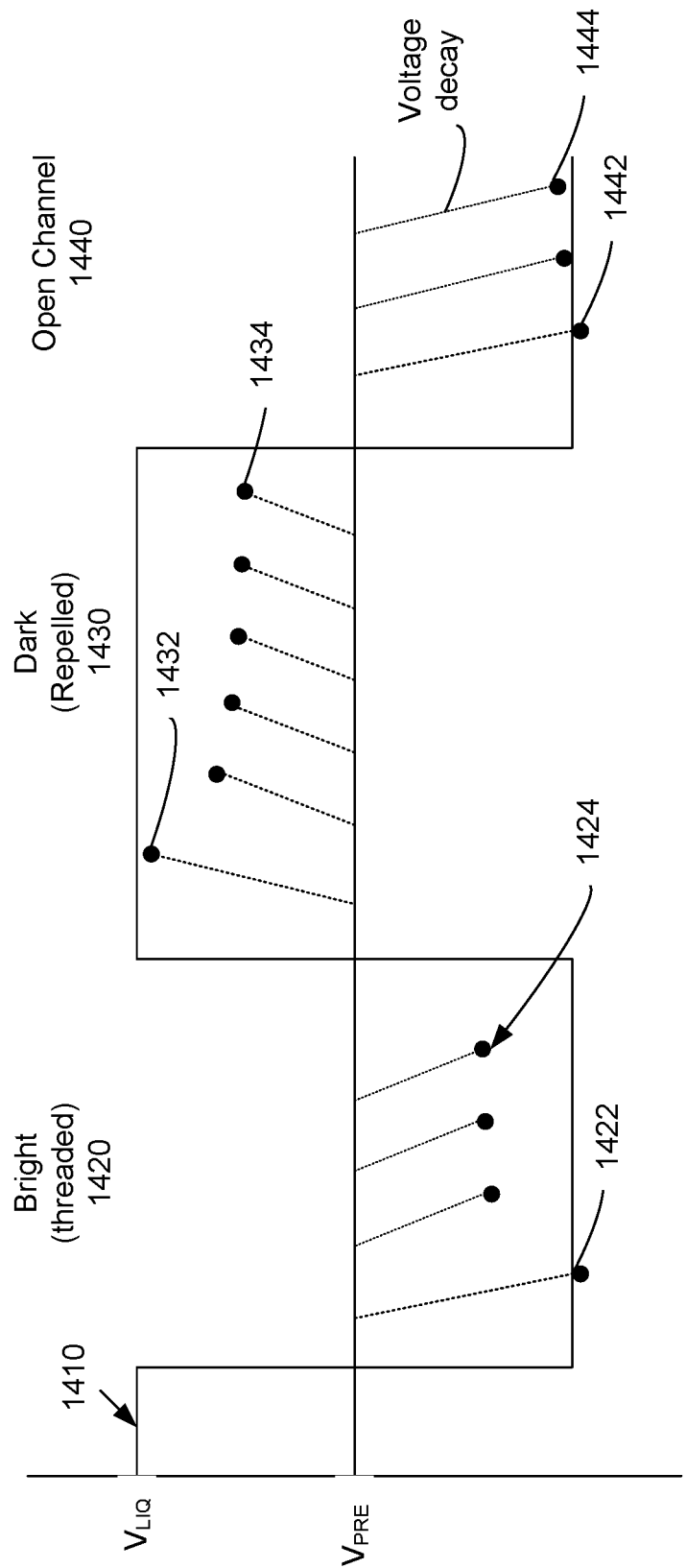
FIG. 14 shows sets of data points for a bright mode of one cycle and for a dark mode of one cycle.

FIG. 14 shows example data points captured from a nanopore cell during bright periods and dark periods of AC cycles. In FIG. 14, the change in the data points is exaggerated for illustration purpose. The voltage ($V_{PRE}$) applied to the working electrode or the integrating capacitor is at a constant level, such as, for example, 900 mV. A voltage signal 1410 ($V_{LIQ}$) applied to the counter electrode of the nanopore cells is an AC signal shown as a rectangular wave, where the duty cycle may be any suitable value, such as less than or equal to 50%, for example, about 40%.

During a bright period 1420, voltage signal 1410 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 1301 is opened, the voltage at a node before the ADC (e.g., at an integrating capacitor) will decrease. After a voltage data point is captured (e.g., after a specified time period), switch 1301 may be closed and the voltage at the measurement node will increase back to $V_{PRE}$ again. The process can repeat to measure multiple voltage data points. In this way, multiple data points may be captured during the bright period.

As shown in FIG. 14, a first data point 1422 (also referred to as first point delta (FPD)) in the bright period after a change in the sign of the $V_{LIQ}$) signal may be lower than subsequent data points 1424. This may be because there is no tag in the nanopore (open channel), and thus it has a low resistance and a high discharge rate. In some instances, first data point 1422 may exceed the $V_{LIQ}$) level as shown in FIG. 14. This may be caused by the capacitance of the bilayer coupling the signal to the on-chip capacitor. Data points 1424 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 1424 may decrease slightly for each measurement due to charge built up at $C_{Double\ Layer}$ 1324, as mentioned below.

During a dark period 1430, voltage signal 1410 ($V_{LIQ}$) applied to the counter electrode is higher than the voltage ($V_{PRE}$) applied to the working electrode, such that any tag would be pushed out of the barrel of the nanopore. When switch 1301 is opened, the voltage at the measurement node increases because the voltage level of voltage signal 1410 ($V_{LIQ}$) is higher than $V_{PRE}$. After a voltage data point is captured (e.g., after a specified time period), switch 1301 may be closed and the voltage at the measurement node will decrease back to $V_{PRE}$ again. The process can repeat to measure multiple voltage data points. Thus, multiple data points may be captured during the dark period, including a first point delta 1432 and subsequent data points 1434. As described above, during the dark period, any nucleotide tag is pushed out of the nanopore, and thus minimal information about any nucleotide tag is obtained, besides for use in normalization. Therefore, the output voltage signals from the cells during the dark period may have little or no use.

FIG. 14 also shows that during bright period 1440, even though voltage signal 1410 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 1442 and subsequent data points 1444, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 1324 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 14.

D. Determining Bases

As part of calibration, various checks can be made during creation of the sequencing cell. Once a cell is created, further calibration steps can be performed, e.g., to identify sequencing cells that are performing as desired (e.g., one nanopore in the cell). Such calibration checks can include physical checks, voltage calibration, open channel calibration, and identification of wells with single nanopore.

Once the usable cells of a chip are identified, a production mode can be run to sequence nucleic acids, one for each usable cell. The ADC values measured during sequencing can be normalized to provide greater accuracy. Normalization can account for offset effects, such as cycle shape and baseline shift. After normalization, embodiments can determine clusters of voltages for the threaded channels, and use the clusters to determine cutoff voltages for discriminating between different bases.

Further details regarding the sequencing operation can be found in, for example, U.S. patent application Ser. No. 14/577,511 entitled "Nanopore-Based Sequencing With Varying Voltage Stimulus," U.S. patent application Ser. No. 14/971,667 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," which are incorporated by reference in their entirety.

IV. Osmotic Imbalance Methods for Stabilizing Nanopores

As discussed above, the nanopores of each sequencing cell can permit the transfer of ions into and out of the well of the sequencing cell. When the bias of the working electrode is positive relative to the counter electrode, negative ions (anions) can be conducted from the external reservoir into the well and positive ions (cations) can be conducted from the well into the external reservoir. When the bias is negative, cations are conducted from the external reservoir into the well and anions are conducted from the well into the external reservoir. Protein pores such as alpha hemolysin (aHL) are known to preferentially conduct either anions or cations and to have unequal conductivity under positive and negative electrical bias. These ion flow properties can lead to a net influx from or efflux into the well. If there is a net flow of ions out of the well as a result of the bias, water will diffuse through the lipid bilayer from the well into the external reservoir to balance their respective electrolyte concentrations. As the volume of fluid in the well is reduced, a resulting strain on the lipid bilayer can cause the inserted nanopore to leave the bilayer. If there is a net flow of ions into the well as a result of the bias, water will diffuse into the well. As the volume of water inside the well increases, the strain on the lipid bilayer can cause additional protein pores to insert into the lipid bilayer. In either case, the net transfer of ions between the well and the external reservoir tends to make a change to the ratio of the well osmolarity to the external reservoir osmolarity.

The nanopores inserted in the planar lipid bilayers (PLBs) have been found to leave the planar lipid bilayers after an extended period of applied either alternating current (AC) or direct current (DC) voltage between the counter electrode and the working electrode. When the applied voltage is significantly reduced, the lifetime of a nanopore inserted in a lipid bilayer is increased. However, a minimum voltage must be applied for tags to thread the nanopore and to measure the presence of the tags in the nanopore. The reduction in nanopore lifetime limits the number of nucleotides in the tag that may be read by the nanopore, thereby reducing the efficiency of the nanopore based sequencing chip.

A. Comparative Example of Ion Efflux from Well Causing Nanopore Instability

Figure 6:
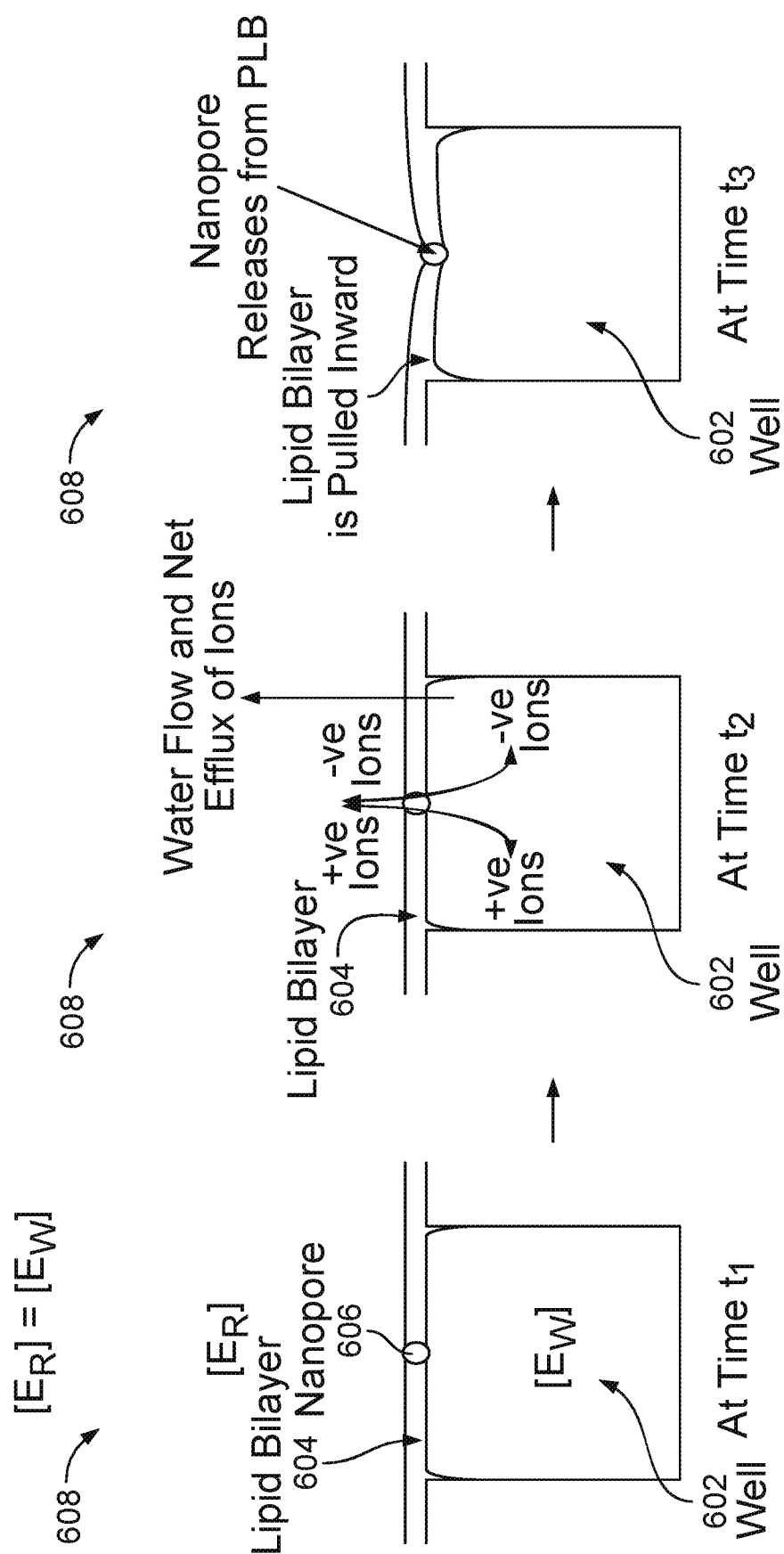
FIG. 6A illustrates that initially at time $t_1$ a nanopore 606 is inserted into a planar lipid bilayer 604 spanning across a well 602 in a cell of the nanopore based sequencing chip.
FIG. 6B illustrates that later at time $t_2$, as a voltage is applied across the lipid bilayer, an osmotic imbalance occurs between the electrolyte solution above and below the lipid bilayer.
FIG. 6C illustrates that later at time $t_3$ a net flow of water across the lipid bilayer places a strain on the lipid bilayer, causing the lipid bilayer to rupture or change its shape to a point at which it fails to work, or causing the nanopore to leave the lipid bilayer.

FIG. 6 (including FIGS. 6A, 6B, and 6C) illustrates an embodiment in which a voltage applied across a lipid bilayer for nucleic acid sequencing over time causes an osmotic imbalance between the electrolyte solution above and below the lipid bilayer, which pulls the lipid bilayer inward into the well and causes the nanopore to be released from the lipid bilayer.

FIG. 6A illustrates that initially at time $t_1$, a nanopore 606 is inserted into a planar lipid bilayer 604 spanning across a well 602 in a cell of the nanopore based sequencing chip. The planar lipid bilayer 604 separates the well from a reservoir 608 external to the well. Initially at time $t_1$, the osmolarity of the salt/electrolyte solution within the well, $[E_w]$, is the same as the osmolarity of the bulk electrolyte solution in the external reservoir, $[E_R]$. Osmolarity, also known as osmotic concentration, is a measure of solute concentration.

FIG. 6B illustrates that later at time $t_2$, as a voltage is applied across the lipid bilayer, an osmotic imbalance between the electrolyte solution above and below the lipid bilayer occurs. In this example, the osmotic imbalance is caused by a net efflux of ions out of the well, which causes water to diffuse out of the well through the lipid bilayer due to osmosis, as will be described in greater detail next.

When a voltage is applied across the lipid bilayer and the nanopore, the nanopore conducts both positive ions (cations) and negative ions (anions) into and out of the well. For example, when an electrolyte solution of potassium chloride (KCl) fills the well and the external reservoir, positive $K^+$ ions and negative $Cl^-$ ions flow into and out of the well. In particular, when the bias of the working electrode is positive relative to the counter electrode, negative ions are conducted from the reservoir into the well and positive ions are conducted from the well into the reservoir. Conversely, when the bias of the working electrode is negative relative to the reference electrode, positive ions are conducted from the reservoir into the well and negative ions are conducted from the well into the reservoir.

Some nanopores, such as alpha hemolysin (aHL), preferentially conduct either anions or cations and have unequal conductivity under positive and negative electrical bias. Because of these properties, a net influx of ions into or a net efflux of ions out of the well can be observed. If there is a net efflux of ions flowing out of the well, then the osmolarity of the salt/electrolyte solution within the well ($[E_w]$) decreases and transiently falls below the osmolarity of the bulk electrolyte solution in the external reservoir ($[E_R]$) (i.e., $[E_w]<[E_R]$), creating an osmolarity gradient across the lipid bilayer. To equilibrate the electrolyte osmolarity in the well and the external reservoir, water diffuses through the planar lipid bilayer from the well into the external reservoir, as shown in FIG. 6B.

FIG. 6C illustrates that later at time $t_3$, a net flow of water across the lipid bilayer places a strain on the lipid bilayer, causing the lipid bilayer to rupture or change its shape to a point that it fails to work or causing the nanopore to leave the lipid bilayer. In this example, the net efflux of ions out of the well causes water to diffuse out of the well, and the resulting loss of water from the well pulls the lipid bilayer inward, causing a change in the shape of the lipid bilayer to a point at which the lipid bilayer fails to work or causing the nanopore to leave the lipid bilayer.

B. Comparative Example of Ion Influx into Well Causing Nanopore Instability

Figure 7:
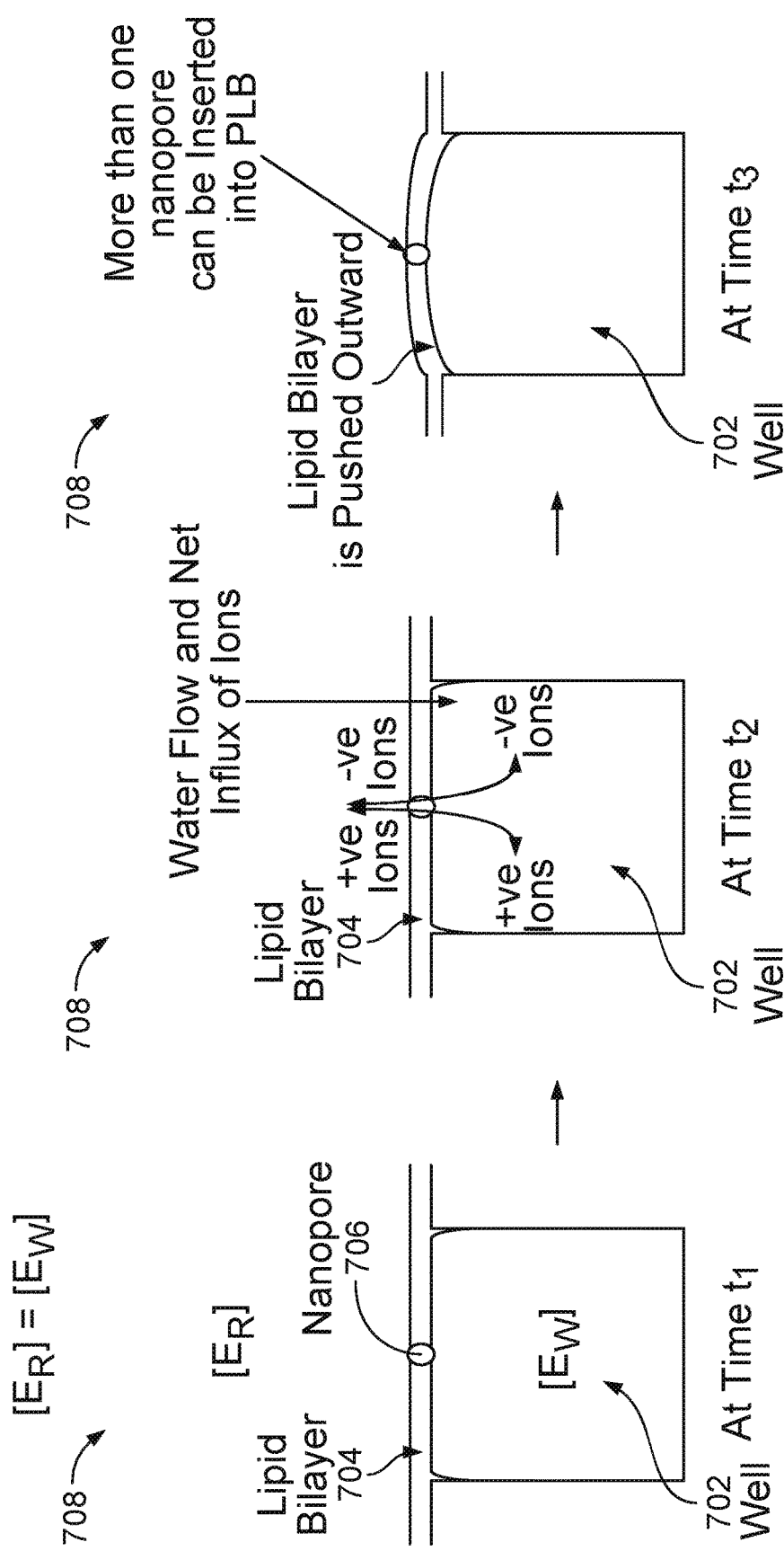
FIG. 7A illustrates that initially at time $t_1$ a nanopore 706 is inserted into a planar lipid bilayer 704 spanning across a well 702 in a cell of the nanopore based sequencing chip.
FIG. 7B illustrates that later at time $t_2$, as a voltage is applied across the lipid bilayer, an osmotic imbalance occurs between the electrolyte solution above and below the lipid bilayer.
FIG. 7C illustrates that later at time $t_3$ a net flow of water across the lipid bilayer and the resulting increase in volume of water in the well push the lipid bilayer outward, causing a change in the shape of the lipid bilayer to a point at which the lipid bilayer fails to work.

FIG. 7 (including FIGS. 7A, 7B, and 7C) illustrates an embodiment in which a voltage applied across a lipid bilayer for nucleic acid sequencing over time causes an osmotic imbalance between the electrolyte solution above and below the lipid bilayer, which pushes the lipid bilayer outward from the well.

FIG. 7A illustrates that initially at time $t_1$, a nanopore 706 is inserted into a planar lipid bilayer 704 spanning across a well 702 in a cell of the nanopore based sequencing chip. The planar lipid bilayer 704 separates the well from a reservoir 708 external to the well. Initially at time $t_1$, the osmolarity of the salt/electrolyte solution within the well ($[E_w]$) is the same as the osmolarity of the bulk electrolyte solution in the external reservoir ($[E_R]$).

FIG. 7B illustrates that later at time $t_2$, as a voltage is applied across the lipid bilayer, an osmotic imbalance between the electrolyte solution above and below the lipid bilayer occurs. In this example, there is a net influx of ions flowing into the well, and the osmolarity of salt/electrolyte solution within the well ($[E_w]$) increases and transiently rises above the osmolarity of the bulk electrolyte solution in the external reservoir ($[E_R]$) (i.e., $[E_w]>[E_R]$), creating an osmolarity gradient across the lipid bilayer. To equilibrate the electrolyte osmolarity in the well and the external reservoir, water diffuses through the planar lipid bilayer from the external reservoir into the well, as shown in FIG. 7B.

FIG. 7C illustrates that later at time $t_3$, a net flow of water across the lipid bilayer and the resulting increase in volume of water in the well pushes the lipid bilayer outward, causing a change in the shape of the lipid bilayer to a point that the lipid bilayer fails to work. As the volume of water inside the well increases, the strain on the planar lipid bilayer may also cause additional nanopores to insert into the lipid bilayer.

C. Counterbalancing Osmotic Imbalances

Figure 8:
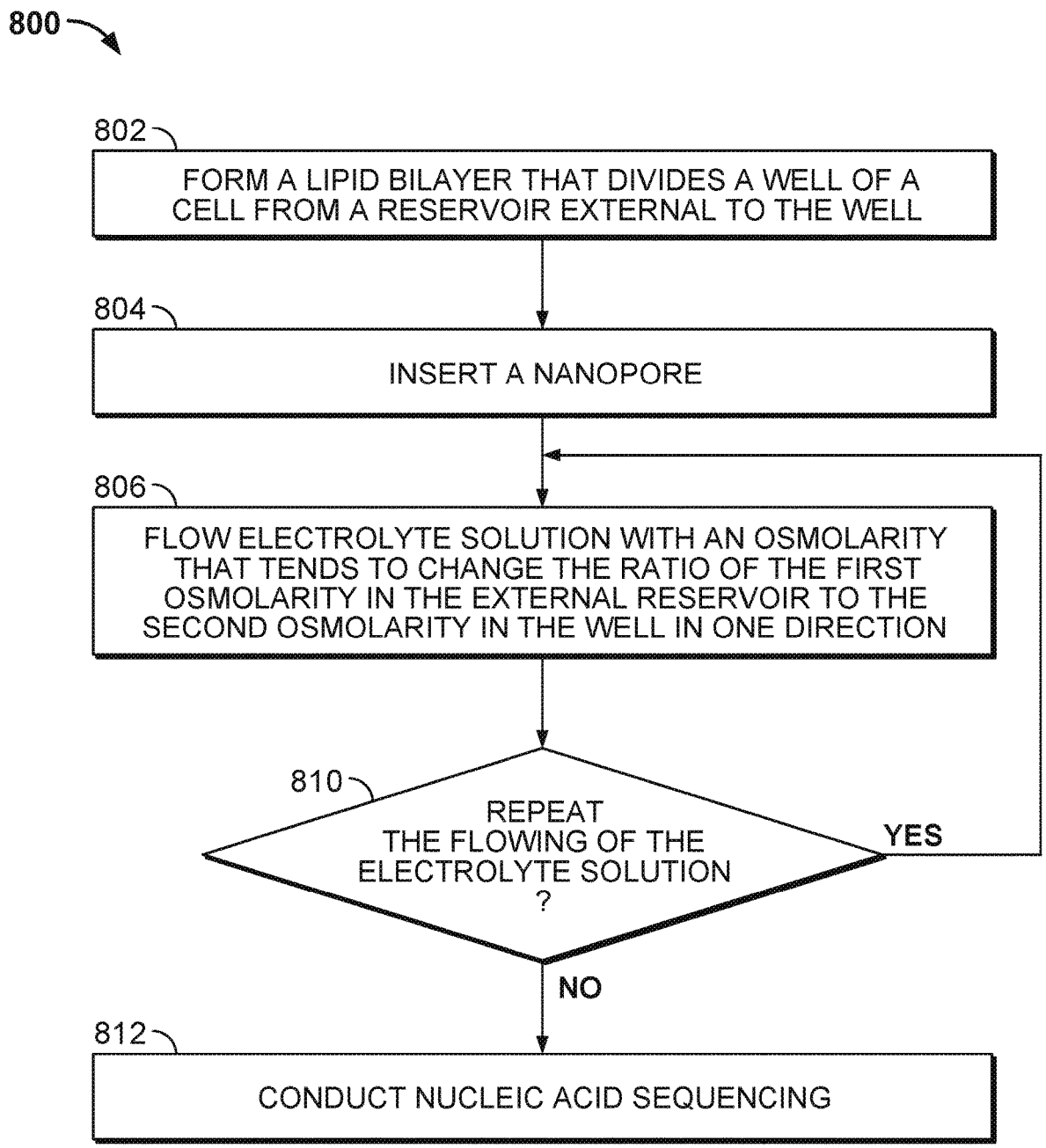
FIG. 8 is a flowchart of a process 800 for an improved technique of extending the lifetime of a nanopore inserted in a lipid bilayer in a cell of a nanopore based sequencing chip for analyzing molecules.

FIG. 8 illustrates an embodiment of a process 800 for an improved technique of extending the lifetime of a nanopore inserted in a lipid bilayer in a cell of a nanopore based sequencing chip for analyzing molecules. The improved technique applies an electrolyte flow over the planar lipid bilayer, wherein the electrolyte flow has a different osmolarity (either a lower or higher osmotic concentration, depending on the net direction of ion transfer through the nanopore) than the osmolarity of the electrolyte below the planar lipid bilayer. In one embodiment, the electrolyte flow over the lipid bilayer is applied prior to or during the application of voltage across the lipid bilayer for nucleic acid sequencing. The disclosed technique has many advantages, including increasing the nanopore lifetime and increasing the efficiency and yield of the nanopore based sequencing chip. It is also appreciated that the disclosed technique can be applied to other semi-permeable membranes (e.g., instead of the lipid bilayer) that permit the transmembrane flow of water but have limited to no permeability to the flow of ions. In some embodiments, the nanopore based sequencing chip used for the process of FIG. 8 includes a plurality of cells 100 of FIG. 1. In some embodiments, the nanopore based sequencing chip used for the process of FIG. 8 includes a plurality of cells 500 of FIG. 5.

In step 802 of process 800, a lipid bilayer is formed in each of the cells of the sequencing chip. The lipid bilayer divides the well of each of the cells from a reservoir external to the well (i.e., a first reservoir). In step 804 of process 800, after a lipid bilayer is formed in a cell a nanopore is inserted into the lipid bilayer. In some embodiments, and as shown in FIG. 8, the nanopore is inserted into the lipid bilayer before an electrolyte solution is flowed to the external reservoir in step 806. In some embodiments, the nanopore is inserted into the lipid bilayer after the electrolyte solution is flowed to the external reservoir. Different techniques can be used to insert nanopores in the cells of the nanopore based sequencing chip. In some embodiments, a solution containing a nanopore forming protein or polypeptide (e.g., α-hemolysin) is flowed through the cells of the nanopore based sequencing chip via the flow chamber such that the solution is flowed above the lipid bilayers. In some embodiments, an agitation or electrical stimulus (e.g., ~100 mV to 1.0 V for 50 ms to 1 s) is applied across the lipid bilayer membrane, causing a disruption in the lipid bilayer and initiating the insertion of an α-hemolysin nanopore into the lipid bilayer.

In step 806 of process 800, a salt/electrolyte buffer solution is flowed through the cells of the nanopore based sequencing chip via the flow chamber. The concentration or osmolarity of the salt electrolyte buffer solution is selected, as described in more detail below, so as to introduce a particular initial osmotic imbalance between the electrolyte solutions above and below the lipid bilayer. This initial osmotic imbalance is characterized by a change to the ratio of the external reservoir (i.e., first reservoir) osmolarity and the well (i.e., second reservoir) osmolarity. In other words, the flowing of the electrolyte solution to the external reservoir tends to make a change to the ratio of the external reservoir osmolarity to the well osmolarity (i.e., an initial osmotic imbalance). The initial osmotic imbalance tends to be substantially canceled out, or counterbalanced, by an opposite osmotic imbalance that is caused by a net transfer of ions through the nanopore during, for example, a subsequent nucleic acid sequencing operation. In the absence of the initial osmotic imbalance, such a net ion transfer can create a structural strain on the lipid bilayer for a time period sufficient to negatively affect the integrity of a nanopore inserted therein. In contrast, with the initial osmotic imbalance acting to substantially counterbalance the effects of a later net ion transfer, such structural strains can be reduced, eliminated, or made more transient, thereby improving the integrity and effective lifetime of the inserted nanopore.

In some embodiments, the distortion of the lipid bilayer as a result of the electrolyte solution flow can have a similar magnitude to the distortion resulting from the application of voltages during sequencing operations, e.g., when a DC voltage is applied. However, the length of time that the distortion driven by the electrolyte solution flow exists can be significantly smaller than the time scale of the sequencing operations. For example, the distortion due to the electrolyte solution flow may exist for only the short time that it takes to establish the osmolarity imbalance, until sequencing starts. As a result, the more transient nature of the distortions causes less structural strain on the lipid bilayers, increasing their stability and integrity, and decreasing the chances of nanopore loss.

In other embodiments, the distortion of the lipid bilayer as a result of the electrolyte solution flow can have a smaller magnitude than the distortion resulting from the application of voltages during sequencing operations, e.g., when AC voltage is applied. For example, the initial distortion (before sequencing) can be slightly outward, at a magnitude of half of the distortion caused by the positive part of the AC signal, but in the opposite direction of distortion. Then, once the AC signal starts (e.g., positive part first), the lipid bilayer can become distorted inward, at half of the magnitude caused by the voltage. Then, the negative part of the AC signal can cause the lipid bilayer to distort outward again (due to the different flux of anions/cations), thereby causing the distortion to be outward again to reach the initial distortion. In this manner, the distortion is never at the full magnitude that would result from the voltage being applied to a cell that had osmolarity balance. Accordingly, in some embodiments, the distortion of the lipid bilayer can match the distortion due to an applied voltage or be less.

For a type of nanopore that is known to produce a net efflux of ions from the well in response to an applied voltage, the osmolarity of the salt/electrolyte solution within the well ($[E_w]$) can be expected to decrease. As a result, the well osmolarity can fall below the osmolarity of the bulk electrolyte solution in the external reservoir ($[E_R]$). In other words, for ion effluxing nanopores, $[E_R]/[E_w]$ can increase and can be >1. To equilibrate the electrolyte osmolarity in the well and the external reservoir, water can be expected to diffuse through the planar lipid bilayer from the well into the external reservoir, as shown previously in FIG. 6B.

To counterbalance the expected increasing $[E_R]/[E_w]$ osmolarity ratio, the concentration or osmolarity of the salt electrolyte buffer solution of step 806 of process 800 is selected as to decrease the $[E_R]/[E_w]$ ratio, changing the ratio in an opposite direction. This can have the effect of driving excess water into the well. For example, the salt electrolyte buffer solution that is flowed through the cells of the nanopore based sequencing chip via the flow chamber at step 806 can have a lower concentration (e.g., 300 mM) than the electrolyte solution that is present in the well (e.g., 340 mM). In response to the lower electrolyte concentration in the solution flowing in the external reservoir (i.e., on the cis side of the planar lipid bilayer), water diffuses across the planar lipid bilayer from the reservoir into the well in order to equalize the concentration on the cis and trans sides of the lipid bilayer. This equalization can take place almost instantaneously since water molecules can readily flow through the planar lipid bilayer. The concentrations on both sides of the planar lipid bilayer can equalize to that of the cis side (e.g., 300 mM) since the volume of the external reservoir is significantly greater than that of the trans side (the well). This can effectively increase the volume of water under the planar lipid bilayer in the well, causing the planar lipid bilayer to bow upwards.

For a type of nanopore that is known to produce a net influx of ions into the well in response to an applied voltage, the osmolarity of the salt/electrolyte solution within the well ($[E_w]$) is expected to increase and transiently rise above the osmolarity of the bulk electrolyte solution in the external reservoir ($[E_R]$) (i.e., $[E_R]/[E_w]$ is decreasing and is <1). To equilibrate the electrolyte osmolarity in the well and the external reservoir, water is expected to diffuse through the planar lipid bilayer from the external reservoir into the well. To counterbalance the expected decreasing $[E_R]/[E_w]$ osmolarity ratio, the concentration or osmolarity of the salt electrolyte buffer solution is determined by process 800 so as to increase the $[E_R]/[E_w]$ ratio, which will in turn force excess water out of the well. For example, the salt electrolyte buffer solution that is flowed through the cells of the nanopore based sequencing chip via the flow chamber in step 806 has a higher concentration (e.g., 340 mM) than the electrolyte solution that is present in the well (e.g., 300 mM). In response to the higher concentration electrolyte solution flowing in the external reservoir (i.e., on the cis side of the planar lipid bilayer), water diffuses across the planar lipid bilayer from the well into the reservoir in order to equalize the concentration on the cis and trans sides of the lipid bilayer. This equalization takes place almost instantaneously since the water molecules readily flow through the planar lipid bilayer. The concentrations on both sides of the planar lipid bilayer equalize to that of the cis side (e.g., 340 mM) since the volume of the external reservoir is significantly greater than that of the trans side (the well). This effectively decreases the volume of water under the planar lipid bilayer in the well, causing the planar lipid bilayer to bow downwards.

The concentration of the electrolyte solution in step 806 of process 800 can be selected based on different factors. The concentration difference between the initial flow and the concentration of the electrolyte solution in the well can, for example, be selected or optimized to maximize nanopore lifetime, limit rapid insertions of nanopores in the planar lipid bilayers, or to avoid rupture of the planar lipid bilayers. In some embodiments, the concentration of the electrolyte solution is selected such that the first change to the osmolarity ratio (caused by the electrolyte solution flow) substantially counterbalances the second change to the osmolarity ratio (caused by the voltage application). In some embodiments, the concentration of the electrolyte solution is selected such that the first change to the osmolarity at least partially counterbalances the second change to the osmolarity ratio. It is appreciated that any first change to the osmolarity ratio that is in an opposite direction to the second change to the osmolarity ratio will be sufficient to at least partially reduce the resulting distortion of the lipid bilayer.

In step 810 of process 800, it is determined whether the flowing of the electrolyte solution (in step 806) should be repeated. Different criteria can be used in this step. In some embodiments, step 806 is performed a predetermined number of times. The concentration of electrolytes in the electrolyte solution can be identical, similar, or different for each iteration of step 806. Lower or higher concentrations of electrolytes can be applied for one or multiple additional cycles. For example, in the case in which the nanopores are known to produce a net efflux of ions from the well, each time step 806 is repeated the concentration of the salt electrolyte solution can be progressively lowered from an initial electrolyte concentration or solution osmolarity (i.e., the conditions for a first iteration of step 806) to a final electrolyte concentration or solution osmolarity (i.e., the conditions for a last iteration of step 806), until the $[E_R]/[E_w]$ ratio is decreased to a predetermined target ratio. This ratio can be estimated by using osmolarity measurements of the external reservoir fluid exiting the system. In the case in which the nanopores are known to produce a net influx of ions into the well, each time step 806 is repeated the concentration of the salt electrolyte solution can be progressively increased from an initial electrolyte concentration or solution osmolarity to a final electrolyte concentration or solution osmolarity until the $[E_R]/[E_w]$ ratio is increased to a predetermined target ratio. If the flowing of the electrolyte solution (in step 806) is repeated, process 800 proceeds to step 806 from step 810; otherwise, process 800 proceeds to step 812.

In FIG. 8, the osmotic imbalance of step 806 of process 800 is shown to be introduced after step 804. In this case, the nanopore is inserted into the lipid bilayer prior to the flowing of the electrolyte solution to adjust an osmotic imbalance, As discussed above, in other embodiments, steps 806 and step 810 can be performed during or before step 804. In these cases, the nanopore is inserted during or after the creation of an osmotic imbalance.

In step 812 of process 800, nucleic acid sequencing is performed as described above. The sequencing operations can include the applying of a voltage across the lipid bilayer, wherein the voltage causes a net transfer of ions between the external reservoir and the well via the nanopore. The ion transfer can make a second change to the ratio of the external reservoir (i.e., first reservoir) osmolarity to the well (i.e., second reservoir) osmolarity. Because of the first change to the osmolarity ratio caused by the electrolyte solution flow of step 806, this second change to the osmolarity ratio is substantially counterbalanced, and the lipid bilayer can return to its original conformation, without significant bowing or distortion. Process 800 can then be repeated for other cycles of introducing an osmotic imbalance through electrolyte flow, and counterbalancing through the application of a voltage during sequencing. In some embodiments, process 800 is operated concurrently with sequencing operations after sequencing has begun. Process 800 can be operated continuously, semi-continuously, or discretely as needed to enhance the effective lifetime or efficiency of the sequencing chip and the lipid bilayers and nanopores therein.

V. Improved Flow Chamber

Process 800 includes steps (e.g., steps 802, 804, and 806) in which different types of fluids (e.g., liquids or gases) are flowed through the cells of the nanopore based sequencing chip via a flow chamber. Multiple fluids with significantly different properties (e.g., compressibility, hydrophobicity, and viscosity) can be flowed over an array of sensor cells (e.g., like cell 100 of FIG. 1 or cell 500 of FIG. 5) on the surface of the nanopore based sequencing chip during this and other processes. The efficiencies of these processes can be improved by exposing each of the sensor cells (also called "sensors") in the array to the fluids in a consistent manner. For example, each of the different types of fluids can be flowed over the nanopore based sequencing chip such that the fluid evenly coats and contacts each of the cells' surfaces before the fluids are delivered out of the chip. As described above, a nanopore based sequencing chip can incorporate a large number of sensor cells configured as an array. As the nanopore based sequencing chip is scaled to include more and more cells, achieving an even flow of the different types of fluids across the cells of the chip becomes more challenging.

In some embodiments, the nanopore based sequencing system that performs process 800 of FIG. 8 includes an improved flow chamber having a serpentine fluid flow channel that directs the fluids to traverse over different sensors of the chip along the length of the channel. The flow channel can, for example, be used to contain the bulk electrolyte 114 in FIG. 1 or the bulk electrolyte 508 in FIG. 5. The flow channel can be used to form external reservoir 522 in FIG. 5, external reservoir 608 in FIG. 6, or external reservoir 708 in FIG. 7.

Figure 9:
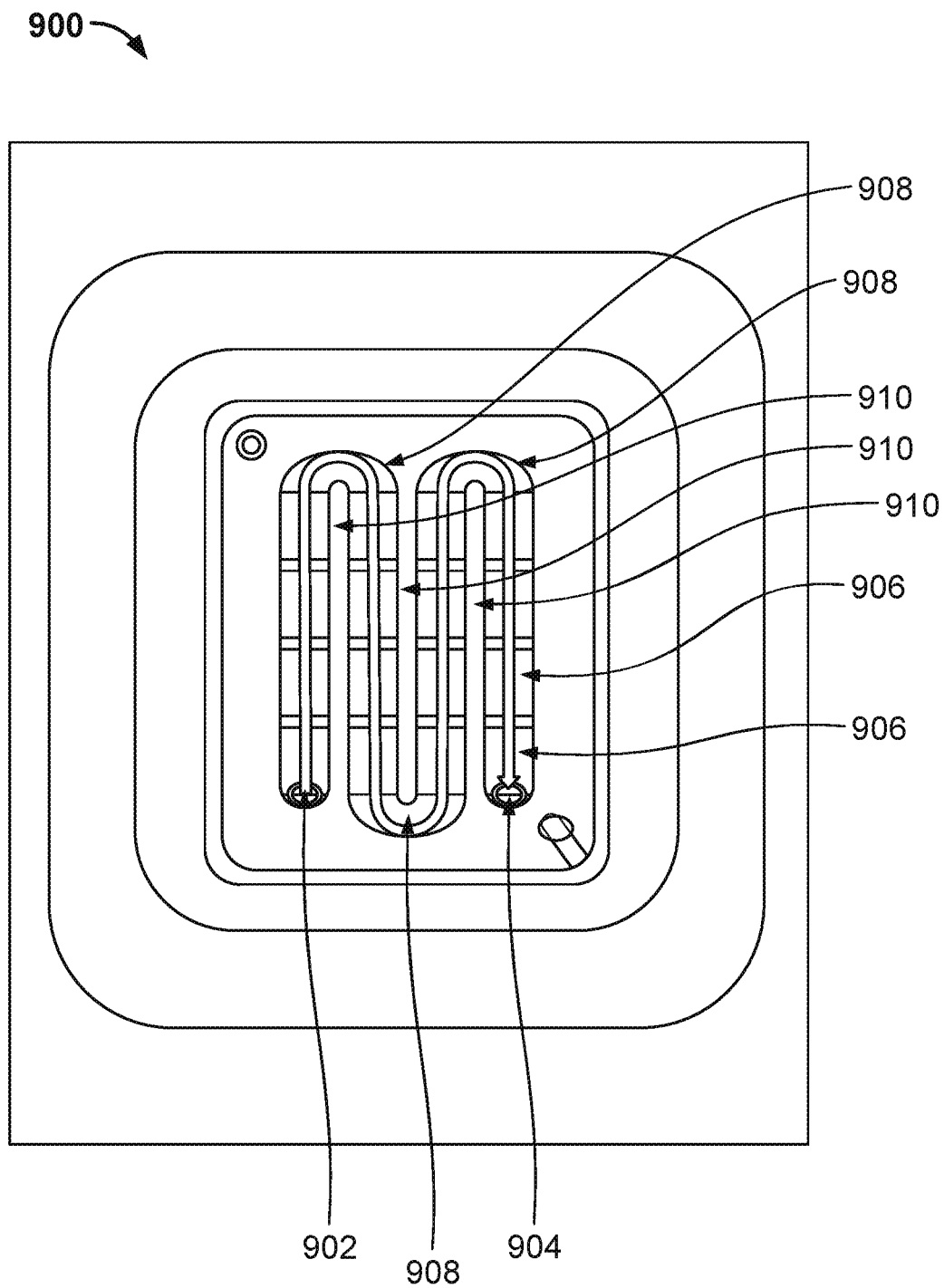
FIG. 9 illustrates the top view of a nanopore based sequencing system 900 with an improved flow chamber enclosing a silicon chip that allows liquids and gases to pass over and contact sensors on the chip surface.

FIG. 9 illustrates the top view of a nanopore based sequencing system 900 with an improved flow chamber enclosing a silicon chip. A serpentine or winding flow channel 908 directs fluids contained within to flow directly above a series of sensor banks 906, e.g., a row or a column of sensors, which can include several thousands of sensor cells, until all of the sensor banks on the chip surface have been traversed at least once. The serpentine configuration of the flow channel allows fluid to: enter the channel through inlet 902, travel along a column or row of sensor banks, repeatedly loop back to travel along an adjacent column or row, and then exit the channel through outlet 904. Each of the sensor banks can include an array of sequencing cells. In some embodiments, each sensor bank includes several thousand sequencing cells.

The type of fluid, the concentration of the fluid, or the flow speed of sequencing system 900 can be selected by a fluidic system controlled by a processor. Inlet 902 can be a tube or a needle. For example, the tube or needle can have a diameter of one millimeter. This is in contrast to alternative embodiments without a serpentine channel, in which the liquid or gas is instead inserted directly into the entire width of the flow chamber. The serpentine channel 908 can be formed by stacking together a top plate and a gasket with dividers 910 that divide the chamber into the serpentine channel to form a flow cell, and then mounting the flow cell on top of the chip. Once the liquid or gas flows through the serpentine channel 908, the liquid or gas can be directed up through outlet 904 and out of system 900.

System 900 allows the fluids to flow more evenly on top of all the sensors on the chip surface. The channel width can be configured to be narrow enough such that capillary action has an effect. More particularly, the surface tension (which is caused by cohesion within the fluid) and adhesive forces between the fluid and the enclosing surfaces can act to hold the fluid together, thereby preventing the fluid or the air bubbles from breaking up and creating dead zones. For example, the channel can have a width of 1 millimeter or less. The narrow channel can enable controlled flow of the fluids and minimize the amount of remnants from a previous flow of fluids or gases.

VI. Forming of Lipid Bilayer

Figure 10:
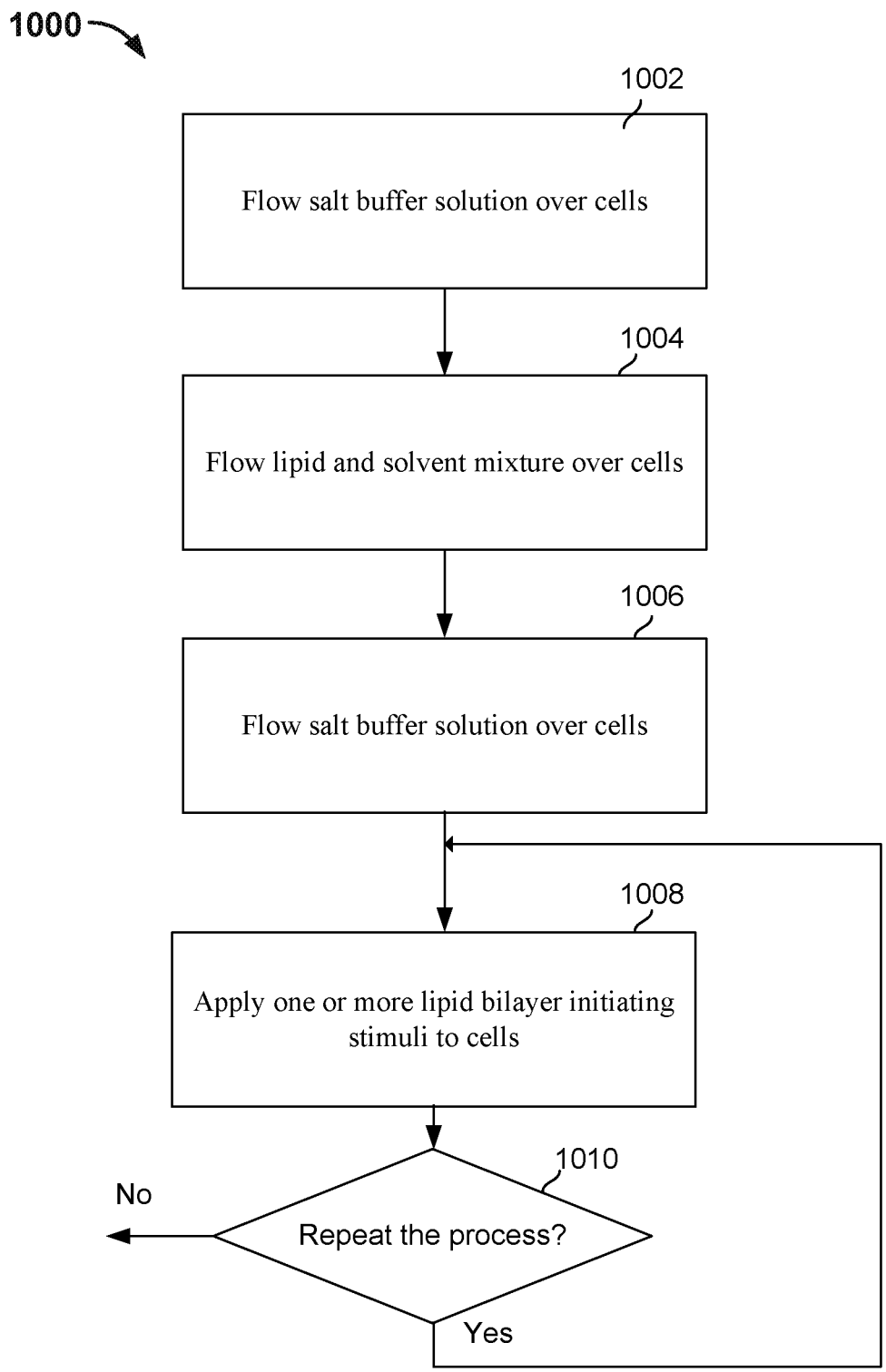
FIG. 10 is a flowchart of a process 1000 for forming the lipid bilayers in the nanopore based sequencing chip.

Different techniques can be used to form the lipid bilayers in the cells of the nanopore based sequencing chip, e.g., as is done in step 802 of process 800. For illustration purposes only, one exemplary process 1000 for forming the lipid bilayers is shown in FIG. 10.

In step 1002 of process 1000, a salt/electrolyte buffer solution is flowed through the cells of the nanopore based sequencing chip via the flow chamber to substantially fill the wells in the cells with the salt buffer solution. As further described herein, the salt buffer solution can include at least one of the following osmolytes: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$).

In one aspect, the present invention provides a concentration of the solution (e.g., salt solution or salt buffer solution) in the well (e.g., 506 in FIG. 5) that is higher than the concentration of solution in the external reservoir (e.g., reservoir 522 in FIG. 5). In another embodiment, the external reservoir is a first reservoir characterized by a first reservoir osmolarity and the well is a second reservoir characterized by a second reservoir osmolarity. In one embodiment, the concentration of solution in the external reservoir is between about 10 nM and 3M. In another embodiment, the concentration of solution in the external reservoir is about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, 305 mM, about 310 mM, about 315 mM, about 320 mM, about 325 mM, about 330 mM, about 335 mM, about 340 mM, about 345 mM, about 350 mM, about 355 mM, about 360 mM, about 365 mM, about 370 mM, about 375 mM, about 380 mM, about 385 mM, about 390 mM, about 395 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1 M, about 1.25 M, about 1.5 M, about 1.75 M, about 2 M, about 2.25 M, about 2.5 M, about 2.75 M, or about 3 M. In another embodiment, the concentration of solution in the well is about 305 mM, about 310 mM, about 315 mM, about 320 mM, about 325 mM, about 330 mM, about 335 mM, about 340 mM, about 345 mM, about 350 mM, about 355 mM, about 360 mM, about 365 mM, about 370 mM, about 375 mM, about 380 mM, about 385 mM, about 390 mM, about 395 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1 M. In one additional embodiment, the concentration of solution in the external reservoir is about 300 mM and the concentration of solution in the well is selected from the group consisting of about 310 mM, about 320 mM, about 330 mM, about 340 mM, about 350 mM, about 360 mM, about 370 mM, about 380 mM, about 390 mM, or about 400 mM. In other embodiments, the concentration of solutions is selected from the group consisting of (i) 300 mM in the external reservoir and 310 mM in the well, (ii) 300 mM in the external reservoir and 320 mM in the well, (iii) 300 mM in the external reservoir and 330 mM in the well, (iv) 300 mM in the external reservoir and 340 mM in the well, (v) 300 mM in the external reservoir and 350 mM in the well, (vi) 300 mM in the external reservoir and 360 mM in the well, (vii) 300 mM in the external reservoir and 370 mM in the well, (viii) 300 mM in the external reservoir and 380 mM in the well, (ix) 300 mM in the external reservoir and 390 mM in the well, and (x) 300 mM in the external reservoir and 400 mM in the well.

In step 1004 of process 1000, a lipid and solvent mixture is flowed through the cells of the nanopore based sequencing chip via the flow chamber. In some embodiments, the lipid and solvent mixture includes lipid molecules such as diphytanoylphosphatidylcholine or 1,2-diphytanoyl-sn-glycero-3-phosphocholine (DPhPC), and 1,2-di-O-phytanyl-sn-glycero-3-phosphocholine (DOPhPC). In some embodiments, the lipid and solvent mixture includes decane or tridecane. When the lipid and solvent mixture is first deposited into the cells to form the lipid bilayers, some of the cells can have lipid bilayers spontaneously formed, but some of the cells can merely have a thick lipid membrane (with multiple layers of lipid molecules and solvent combined together) spanning across each of the wells of the cells.

In step 1006 of process 1000, a salt/electrolyte buffer solution is flowed through the cells of the nanopore based sequencing chip via the flow chamber to substantially fill the external reservoir with the salt buffer solution.

In step 1008, in order to increase the yield of the nanopore based sequencing chip (i.e., the percentage of cells in the nanopore based sequencing chip with properly formed lipid bilayers and nanopores), one or more types of lipid bilayer initiating stimuli can be applied to the nanopore based sequencing chip to facilitate the formation of lipid bilayers in additional cells. One or more types of lipid bilayer initiating stimuli can be applied simultaneously, or in different orders, during a lipid bilayer initiating stimulus phase (step 1008), which can be repeated (determined by step 1010) a plurality of times.

A lipid bilayer initiating stimulus facilitates the creation of a small lipid bilayer on a thick lipid membrane. Once a small transient lipid bilayer on a thick lipid membrane is formed, the application of additional lipid bilayer initiating stimuli acts as a positive feedback to continue to enlarge the surface area of the lipid bilayer. As a result, the time required to form lipid bilayers in the cells of the nanopore based sequencing chip can be significantly reduced. One type of lipid bilayer initiating stimulus is a mechanical stimulus, such as a vibration stimulus. Another type of lipid bilayer initiating stimulus is an electrical stimulus. Those of ordinary skill in the art will appreciate that other types of stimulus may be suitable for use with the present invention. Another type of lipid bilayer initiating stimulus is a physical stimulus. For example, flowing a salt/electrolyte buffer solution through the cells of the nanopore based sequencing chip via a flow chamber facilitates the formation of a lipid bilayer over each of the cells. The salt buffer solution flowed over the cells facilitates the removal of any excess lipid solvent such that the thick lipid membranes can be thinned out and transitioned into lipid bilayers more efficiently.

VII. Benefits of Counterbalancing Osmotic Imbalances

The provided counterbalancing osmotic imbalance methods and systems offer several benefits that can include increased longevity of nanopores and sequencing cells, greater percentages of functional cells within sequencing arrays, and higher efficiencies of instruments. These benefits arise from the ability of the osmotic imbalance to counteract the potentially destructive effects of ion and water flow between the two sides of the lipid bilayer, which in the absence of counterbalancing can add conformational stress to the bilayer and cause rupture or nanopore loss as described further in the illustrations below A. Illustration of Prevention of Ejection of Pore FIG. 11A illustrates that by flowing over a lipid bilayer at time $t_1$ a lower concentration of electrolyte solution than is initially present in the well while the planar lipid bilayer is in place between the well and the external reservoir, excess water is forced into the well, causing the planar lipid bilayer to bow upwards. As discussed above, since (1) water can diffuse across the planar lipid bilayers, (2) ions can pass through the nanopores, and (3) the salt electrolyte buffer solution that is flowed through the cells can introduce different osmolytes into the external reservoir over time, both the volume and the osmolyte content of the liquid held in the external reservoir and the wells can change over time. It is recognized that the external reservoir can be characterized by a first reservoir osmolarity, which is the osmolarity of the liquid contained in the external reservoir at a specific time. A well in a cell can also be characterized by a second reservoir osmolarity, which is the osmolarity of the liquid contained in the well and confined by the lipid bilayer at a specific time.

FIG. 11B illustrates that the volume of water forced into the well at time $t_1$ (FIG. 11A) due to the initial flow of lower concentration electrolyte acts to substantially counterbalance a volume of water removed from the well at a later time $t_2$. The removal of water from the well at time $t_2$ can be, for example, as a result of voltage applied during sequencing operation described above. Because the methods and systems described herein create an osmotic imbalance that substantially counterbalances the effects of such a voltage application, the "pre-bowed" well is capable of withstanding the removal of a larger volume of water before the planar lipid bilayer ruptures or the nanopore inserted therein is forced to exit.

FIG. 11C illustrates that in a comparative method lacking the application of a counteracting osmotic imbalance, the volume of water removed from the well at a later time $t_2$ can be sufficiently large so as to disrupt the lipid bilayer or eject its inserted nanopore. In the figure it can be seen that the inward bowing of the bilayer releases the nanopore, ending the effectiveness of the cell for use in sequencing operations. This is in contrast to the illustration of FIG. 11B, in which the outward and inward bowing caused by the electrolyte flow and the voltage application, respectively, substantially cancel one another out, leaving the nanopore and lipid bilayer intact.

Figure 12A:
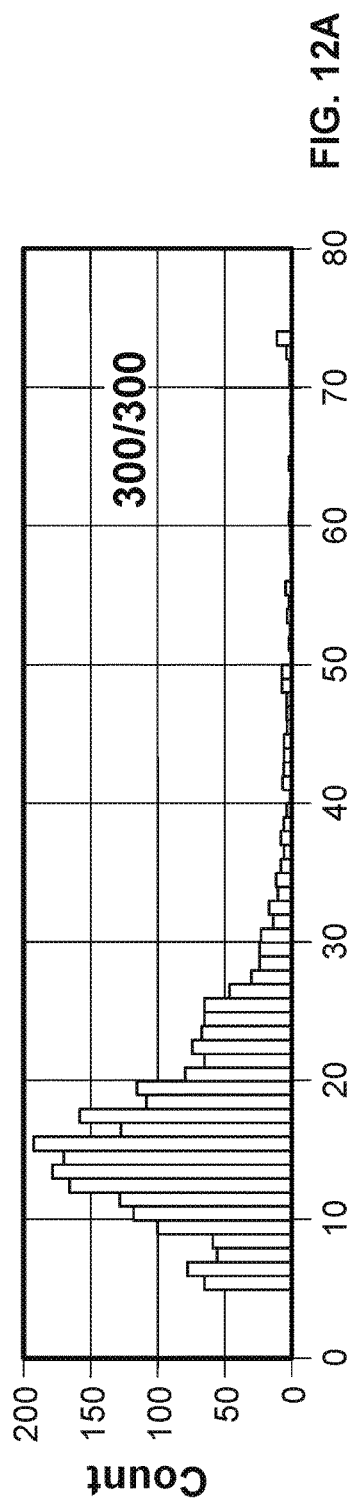
FIG. 12A illustrates the average nanopore lifetime for a comparative method in which the external reservoir and well osmolarities are both 300 mM.
Figure 12B:
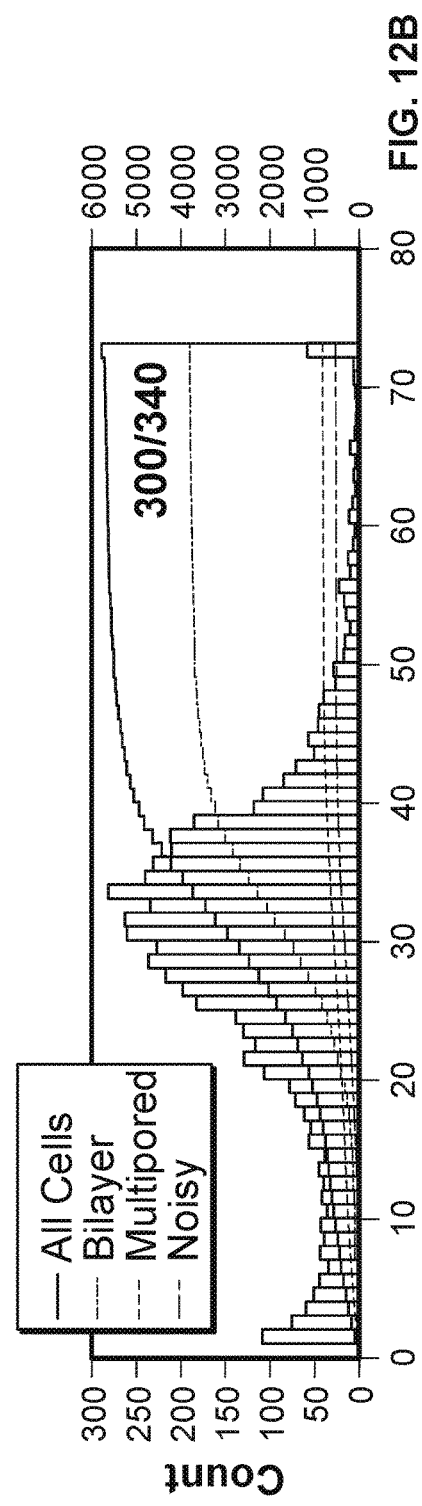
FIG. 12B illustrates the average nanopore lifetime for a method in accordance with an embodiment in which the external reservoir osmolarity is 300 mM and the well osmolarity is 340 mM.
Figure 12C:
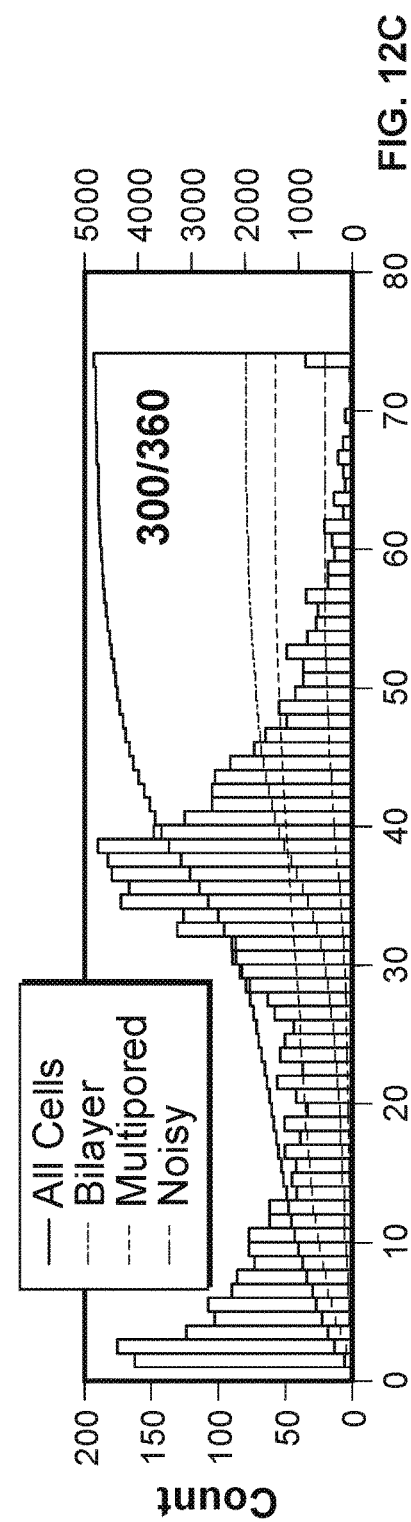
FIG. 12C illustrates the average nanopore lifetime for a method in accordance with an embodiment in which the external reservoir osmolarity is 300 mM and the well osmolarity is 360 mM.

B. Example of Increasing Effective Nanopore Lifetime with Counterbalancing Osmatic Imbalances FIGS. 12A, 12B, and 12C illustrate that using process 800, the average lifetime of a nanopore in a cell is significantly increased. For each chart, the y-axis represents the number of nanopores, and the x-axis represents the lifetime of the nanopores in units of 100 seconds as observed during sequencing operations. In FIG. 12A, the concentrations of both the electrolyte solution that is flowed through the cells of the sequencing chip via the flow chamber, and the electrolyte solution in the well are 300 mM. As shown in the graph, the average lifetime of the nanopores is around 1500 seconds. This corresponds with a comparative method (as in, for example, FIG. 11C), in which no osmotic imbalance is applied prior to sequencing, and nanopore loss can be occurring through bilayer distortion brought about by voltage applications.

In the graph of FIG. 12B, the concentration of the electrolyte solution that is flowed through the cells of the nanopore based sequencing chip via the flow chamber is 300 mM, and the concentration of the electrolyte solution in the well is 340 mM. This corresponds with a method in which an osmotic imbalance is applied, water will be driven into the wells to equilibrate osmolyte concentrations, and the bilayer will "pre-bow" outward and substantially counterbalance bilayer distortion brought about by voltage applications (as in, for example, FIGS. 11A and 11B). The average lifetime of the nanopores in this case is increased to around 3200 seconds.

In the graph of FIG. 12C, the concentration of the electrolyte solution that is flowed through the cells of the nanopore based sequencing chip via the flow chamber is 300 mM and the concentration of the electrolyte solution in the well is 360 mM. The average lifetime of the nanopores is further increased to around 3800 seconds. This also corresponds with a method in similar to that producing the results of the FIG. 12B graph, but with the creation of a larger osmotic imbalance that further improves the nanopore effective lifetime. Such experimentation can be continued in an iterative fashion to empirically derive or optimize electrolyte concentrations that are effective in improving nanopore stability and sequencing cell robustness.

VIII. Computer System

Figure 15:
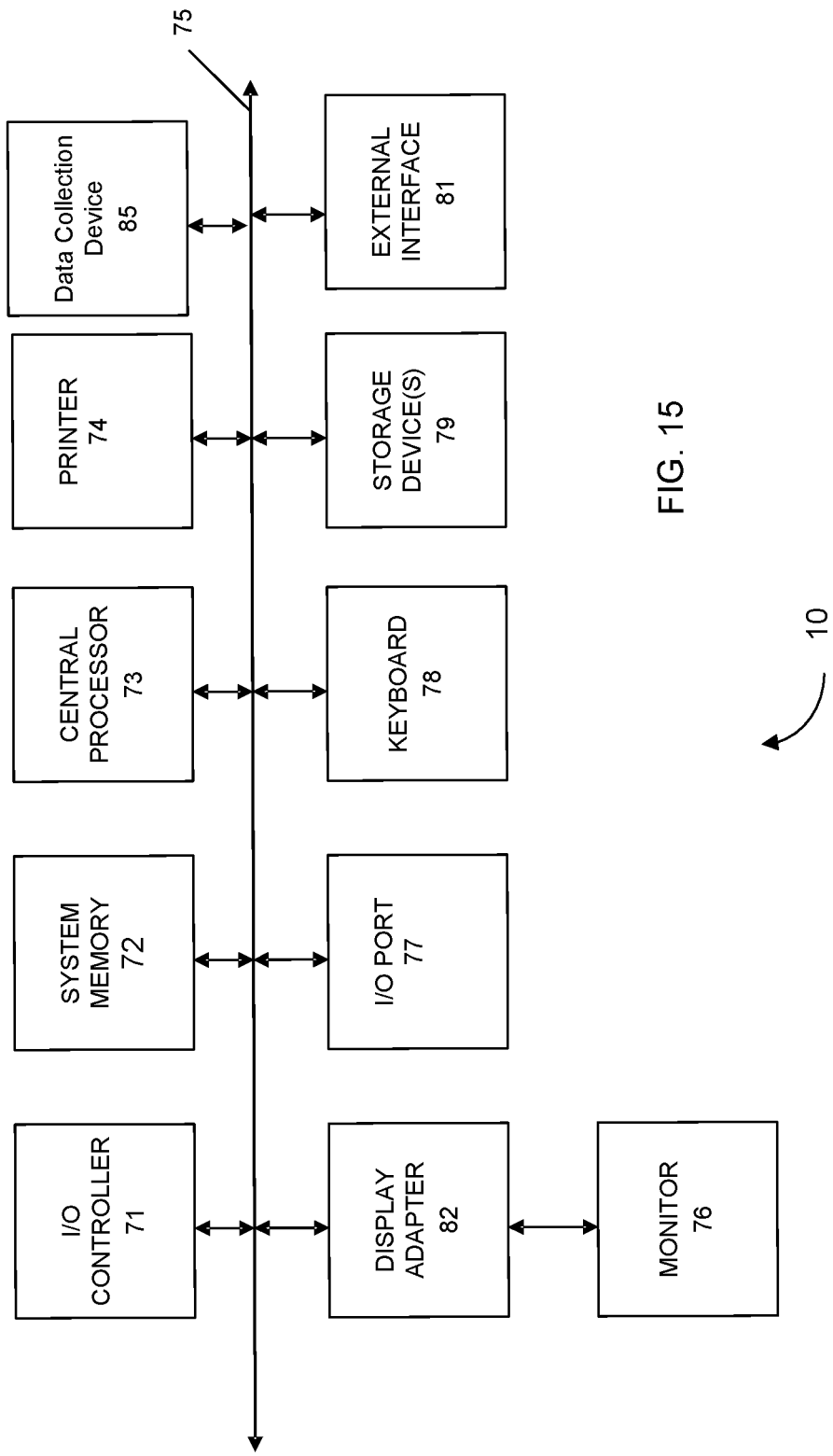
FIG. 15 shows a block diagram of an example computer system usable with systems and methods according to embodiments.

Any of the computer systems mentioned herein can utilize any suitable number of subsystems. Examples of such subsystems are shown in FIG. 15 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 15 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FIREWIRE®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

Although the foregoing embodiments have been described in some detail for purposes of clarity of understanding, the invention is not limited to the details provided. There are many alternative ways of implementing the invention. The disclosed embodiments are illustrative and not restrictive. The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated. The terms "first" and "second" when used herein with reference to elements or properties are simply to more clearly distinguish the two or more elements or properties and unless stated otherwise are not intended to indicate order.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

All patents, patent applications, publications, and descriptions mentioned herein are incorporated by reference in their entirety for all purposes. None is admitted to be prior art.

What is claimed is:

1. A system for analyzing molecules, the system comprising:
   a sequencing chip comprising an array of cells, wherein each of the cells comprises a well;
   a reservoir coupled to the sequencing chip; and
   a processor or a circuitry configured to:
      form a lipid bilayer that divides the reservoir from the well of one of the array of cells, wherein the reservoir has a first reservoir osmolarity, and wherein the well has a second reservoir osmolarity;
      flow an electrolyte solution to the reservoir, wherein the electrolyte solution has an electrolyte solution osmolarity that differs from the first reservoir osmolarity, thereby making a first change to a ratio of the first reservoir osmolarity to the second reservoir osmolarity; and
      apply a voltage across the lipid bilayer, wherein the lipid bilayer includes a nanopore, and wherein the voltage causes a net transfer of ions between the reservoir and the well, thereby making a second change to the ratio of the first reservoir osmolarity to the second reservoir osmolarity, wherein the first change to the ratio and the second change to the ratio substantially counterbalance each other.

2. The system of claim 1, wherein the net transfer of ions between the reservoir and the well comprises a net efflux of ions from the well to the reservoir.

3. The system of claim 2, wherein the net efflux of ions from the well to the reservoir increases the ratio of the first reservoir osmolarity to the second reservoir osmolarity, and wherein flowing the electrolyte solution to the reservoir decreases the ratio of the first reservoir osmolarity to the second reservoir osmolarity.

4. The system of claim 3, wherein the electrolyte solution osmolarity is lower than the second reservoir osmolarity before the electrolyte solution is flowed to the reservoir.

5. The system of claim 4, wherein the processor or the circuitry is further configured to:
   progressively reduce the electrolyte solution osmolarity from an initial electrolyte solution osmolarity to a final electrolyte solution osmolarity to make the first change to the ratio of the first reservoir osmolarity to the second reservoir osmolarity.

6. The system of claim 1, wherein the net transfer of ions between the reservoir and the well comprises a net influx of ions into the well from the reservoir.

7. The system of claim 6, wherein the net influx of ions into the well from the reservoir decreases the ratio of the first reservoir osmolarity to the second reservoir osmolarity, and wherein flowing the electrolyte solution to the reservoir increases the ratio of the first reservoir osmolarity to the second reservoir osmolarity.

8. The system of claim 7, wherein the electrolyte solution osmolarity is higher than the second reservoir osmolarity before the electrolyte solution is flowed to the reservoir.

9. The system of claim 8, wherein the processor or the circuitry is further configured to progressively increase the electrolyte solution osmolarity from an initial electrolyte solution osmolarity to a final electrolyte solution osmolarity to make the first change to the ratio of the first reservoir osmolarity to the second reservoir osmolarity.

10. The system of claim 1, wherein the processor or the circuitry is further configured to insert the nanopore into the lipid bilayer before the electrolyte solution is flowed to the reservoir.

11. The system of claim 1, wherein the processor or the circuitry is further configured to insert the nanopore into the lipid bilayer after the electrolyte solution is flowed to the reservoir.

12. The system of claim 1, wherein the lipid bilayer spans across the well, wherein the reservoir is external to the well, wherein the reservoir has a reservoir volume, wherein the well has a well volume, and wherein the reservoir volume is larger than the well volume.

13. The system of claim 1, wherein the voltage applied across the lipid bilayer is an alternating current voltage.

14. The system of claim 1, wherein the voltage applied across the lipid bilayer is a direct current voltage.

* * * * *